US011608508B2

(12) United States Patent
Tabuchi

(10) Patent No.: US 11,608,508 B2
(45) Date of Patent: Mar. 21, 2023

(54) METHOD FOR ESTABLISHING MODIFIED HOST CELL

(71) Applicant: CHUGAI SEIYAKU KABUSHIKI KAISHA, Tokyo (JP)

(72) Inventor: Hisahiro Tabuchi, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/434,514

(22) PCT Filed: Oct. 10, 2013

(86) PCT No.: PCT/JP2013/077629
§ 371 (c)(1),
(2) Date: Apr. 9, 2015

(87) PCT Pub. No.: WO2014/058025
PCT Pub. Date: Apr. 17, 2014

(65) Prior Publication Data
US 2015/0275230 A1 Oct. 1, 2015

(30) Foreign Application Priority Data
Oct. 10, 2012 (JP) .............................. JP2012-225537

(51) Int. Cl.
C12N 15/85 (2006.01)
C12N 15/113 (2010.01)
C12P 21/00 (2006.01)
C12P 21/02 (2006.01)

(52) U.S. Cl.
CPC ............ *C12N 15/85* (2013.01); *C12N 15/113* (2013.01); *C12P 21/00* (2013.01); *C12N 2310/14* (2013.01); *C12N 2310/141* (2013.01); *C12N 2330/51* (2013.01); *C12P 21/02* (2013.01)

(58) Field of Classification Search
CPC .................................................... C12N 15/85
See application file for complete search history.

(56) References Cited

U.S. PATENT DOCUMENTS

| 2009/0191591 A1 | 7/2009 | Tabuchi et al. |
| 2010/0167346 A1 | 7/2010 | Tabuchi et al. |
| 2010/0233759 A1 | 9/2010 | Tabuchi et al. |
| 2011/0014654 A1 | 1/2011 | Tabuchi et al. |
| 2014/0030758 A1 | 1/2014 | Tabuchi et al. |

FOREIGN PATENT DOCUMENTS

| EP | 2011880 A1 | 1/2009 |
| EP | 2135946 A1 | 12/2009 |
| EP | 2186905 A1 | 5/2010 |
| EP | 2194126 A1 | 6/2010 |
| EP | 2213746 A1 | 8/2010 |
| EP | 2695947 A1 | 2/2014 |
| JP | 2012-055303 A | 3/2012 |
| WO | WO 2007/119774 A1 | 10/2007 |
| WO | WO 2008/114673 A1 | 9/2008 |
| WO | WO 2009/020144 A1 | 2/2009 |
| WO | WO 2009/054433 A1 | 4/2009 |
| WO | WO 2012/137683 A1 | 10/2012 |

OTHER PUBLICATIONS

Stiefel et al (Pharm. Bioprocess, 3(3); 227-247, 2015).*
Takasaki (Methods Mol Biol. 2013;942:17-55).*
Martinez-Sanchez et al (Biology 2013, 2, 189-205).*
Warzocha et al (Leukemia and Lymphoma, Val. 24. pp. 267-281, 1997).*
Lan et al., "Suppression of IκBα increases the expression of matrix metalloproteinase-2 in human ciliary muscle cells," Molecular Vision, Sep. 26, 2009, 15:1977-1987.
Lei et al., "Regulation of NF-κB inhibitor IκBα and viral replication by a KSHV microRNA," Nature Cell Biology, Feb. 2010, 12(2):193-199.
Arenzana-Seisdedos et al., "Inducible Nuclear Expression of Newly Synthesized IκBα Negatively Regulates DNA-Binding and Transcriptional Activities of NF-κβ," Molecular and Cellular Biology, May 1995, 15(5):2689-2696.

* cited by examiner

*Primary Examiner* — Anoop K Singh
*Assistant Examiner* — Magdalene K Sgagias
(74) *Attorney, Agent, or Firm* — Foley & Lardner LLP

(57) ABSTRACT

An object of the present invention is to establish a cell line that is useful as a host cell for use in recombinant protein production, highly expresses transgenes stably, and grows stably.
The present invention provides a method for establishing a cell line for recombinant protein production capable of stably expressing two or more foreign genes, comprising transferring a gene of a non-coding RNA suppressing the expression of NfkBia to a cell.

4 Claims, 35 Drawing Sheets

Specification includes a Sequence Listing.

☐ 1- Strongly MAb1 (anti-IL-6R antibody)-expressing DXB11s cell (Hy-Fish addition)

☐ 2- Strongly MAb1 (anti-IL-6R antibody)-expressing DXB11s cell (porcine lysate addition)

Figure 12

A part of Hamster Nfkbia mRNA (134 bp)

```
         10        20        30        40        50
agtacccggatacagcagcagctgggccagctgacccgggaaaatcttca 60        70        80        90       100
gatgctgcccgagagtgaggatgaggagagctacgacacagagtcagaat 110       120       130
tcacggaggatgagctgccctatgatgactgtgt
```
SEQ ID NO: 36

TaqMan Probe Set for Hamster Nfkbia mRNA

| | | |
|---|---|---|
| 5'- cagctgacccgggaaaatc | Tm 59°C  19mer | SEQ ID NO: 20 |
| 5'- tgactctgtgtcgtagctctcctc | Tm 59°C  24mer | SEQ ID NO: 21 |
| 5'- FAM-tcagatgctgcccgagagtgagga-TAMRA | Tm 68°C  24mer | SEQ ID NO: 22 |

| | | |
|---|---|---|
| 1- | TAUT-overexpressing | DXB11s cell |
| 2- | CSAD-overexpressing | DXB11s cell |
| 3- Strongly MAb2 (anti-glypican 3 antibody)-expressing | | DXB11s cell |
| 4- Strongly MAb2 (anti-glypican 3 antibody)-expressing and TAUT-overexpressing | | DXB11s cell |

Figure 14 ctctgggctcgaatggcatgggggacagcttttatatggttaactccgcccgttttatgactagaaccaatagttttaatgccaaa
tgcactgaaatcccctaatttgcaaagccaaacgcccccctatgtgagtaatacggggactttttacccaatttcccaagcggaaa
gcccccctaatacactcatatggcatatgaatcagcacggtcatgcactctaatggcggcccatagggactttccacatagggg
gcgttcaccatttcccagcatagggggtggtgactcaatggcctttacccaagtacattgggtcaatgggaggtaagccaatgg
gtttttccattactggcaagcacactgagtcaaatgggactttccactgggttttgcccaagtacattgggtcaatgggaggtga
gccaatgggaaaaacccattgctgccaagtacactgactcaatagggactttccaatgggttttccattgttggcaagcatata
aggtcaatgtgggtgagtcaatagggactttccattgtattctgcccagtacataaggtcaataggggggtgaatcaacaggaaa
gtcccattggagccaagtacactgcgtcaatagggactttccattgggttttgcccagtacataaggtcaataggggatgagtc
aatgggaaaaacccattggagccaagtacactgactcaatagggactttccattgggttttgcccagtacatagggtcaatagg
gggtgagtcaacaggaaagttccattggagccaagtacattgagtcaatagggactttccaatgggttttgcccagtacataag
gtcaatgggaggtaagccaatgggttttcccattactggcacgtatactgagtcattagggactttccaatgggttttgcccagt
acataaggtcaataggggtgaatcaacaggaaagtcccattggagccaagtacactgagtcaatagggactttccattgggttt
tgcccagtacaaaaggtcaatagggggtgagtcaatgggttttcccattattggcacgtacataaggtcaataggggtgagtc
attgggttttccagccaatttaattaaaacgccatgtactttcccaccattgacgtcaatgggctattgaaactaatgcaacgtga
cctttaaacggtactttccatagctgattaatgggaaagtaccgttctcgagccaatacacgtcaatgggaagtgaaagggca
gccaaaacgtaacaccgccccggttttcccctggaaattccatattggcacgcattctattggctgagctgcgttctacgtgggt
ataagaggcgcgaccagcgtcggtaccgtcgcagtcttg

SEQ ID NO: 23

Figure 18

| MAb1-producing cell line | Maximum viable cell density (x10e6 cells/mL) | mAb yield (g/L/14 days) |
|---|---|---|
| APES165-overexpressing cell line | 11.5 ±1.7 | 4.4±0.6 |
| ALT1-overexpressing cell line | 8.9 ±1.8 | 4.0±0.6 |
| Parent cell line | 4.1 | 3.4 |

Shaker fed-batch culture (n=3)

Figure 24

```
>gb|JH001217.1| Query1 on Cricetulus griseus cell line CHO-K1 unplaced genomic scaffold
scaffold4235, whole genome shotgun sequence Length=486540 Score = 378 bits (418), Expect = 3e-102
Identities = 352/440 (80%), Gaps = 33/440 (7%) Strand=Plus/Minus Query  3       TGTCTGTAAAAATCTGTTTAATAAATATACATCTTAGAAGTACCAAAATAATTACCAACA  62      (AI462015)
               ||||||||||||||||||||||||||||||||||||||||||||||||||||||||||||
Sbjct  385673  TGTCTGTAAAAATCTGTTTAATAAATATACATCTTAGAAGTACCAAAATAATTACCAACA  385614  (CHO-K1 genome)

Query  63      AAATACAACATATACAACATTTACAAGAAGGCGACACAGACCTTAGTTGGGGCGACTTT   122     (AI462015)
               |||||||  ||||||||||||||||||| ||  |  | ||| ||| ||| ||| | ||||
Sbjct  385613  AAATACACCATATACAACATTTACAAGAGGGTAACAAAAACCTCAGTCGGGAGTGACT--  385556  (CHO-K1 genome)

Query  123     TAAGCACATGCCACTGAACACCTGGCTCTTACATGGGAGGACACACTGGGCTCACTTACT  182     (AI462015)
               ||||||| ||||| ||||||||||||| | |||||| |||||||||| |||||| |||
Sbjct  385555  --AGCACATACCACTCAACACCTGGTTC-TACATGTGAGGACATACCAGGCTCAGCTACC  385499  (CHO-K1 genome)

Query  183     AGGTCTATGGTGGTTCAATCAAAAGCACAATAAATAAAACGTGGT-CCTTTCATTAGGTT  241     (AI462015)
               || |||| ||||| |||||||||||||||||||| | || ||||||||||| || |
Sbjct  385498  AGATCTA---CCGTTCAGTCAAAAGCACAATAAATAGAATGTGGTCCCTTTCATCAG--T  385444  (CHO-K1 genome)

Query  242     CTGGAAAATCACCTccccccccccaaaaaaaaTCCCACAAACATGAACCTTAAGAGACA  301     (AI462015)
               ||||||| |||||||||         ||||| | ||| | |||| | ||||||||||||
Sbjct  385443  CTGGAAAACCACCTCCC-----------AAAACCTCACGAATGTGAGCTTAAAAGACA  385396  (CHO-K1 genome)

Query  302     TTTTCTTTGAATTTCAGTGATCTGTTTCCCCGGATTTCACAAAGACAACA----GCCGAA  357     (AI462015)
               ||||||||||||| || |||||||||||||||  || ||||||| |||| ||  ||
Sbjct  385395  TTTTCTTTGAATTCCAATGATCTGTTTCCCC--ATTTCACAAAAATAACAATCTGCC--A  385340  (CHO-K1 genome)

Query  358     TCACCCCAGTAAAATGCCTGGGTCTAGGCGCTGTGTGGTGTGGTGCTAAGTATA-CCCTT  416     (AI462015)
               ||||| ||||| |||| |||| |||| |||| |||||||||||| ||||||| |||||
Sbjct  385339  TCACCAGAGTAAGATGCTTGGGGGCAGGCTGTGTGCAGTGTGGTGGTAAGTATATCCCTT  385280  (CHO-K1 genome)

Query  417     TC-TCAttttttttttttttt  435
               || | |||||||||||| ||
Sbjct  385279  TCTTTCTTTTTTTTCTTCTT  385260
```

SEQ ID NO: 40

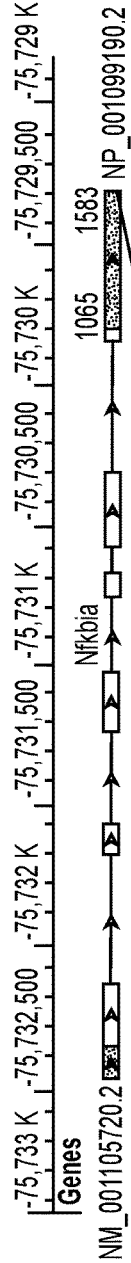
FIG. 25A
FIG. 25B

FIG. 25C

```
Genes
XM_522823.3  -34,335,500  -34,335 K  -34,334,500  -34,334 K  -34,333,500  -34,333 K  -34,332,500  -34,332 K  -34,331,500  -34,331 K
                                                              NFKBIA                    1711  2228
                                                                                              XP_522823.2

Chimpanzee Nfkbia  2209 : TGTAAAAAATC TGTTTAATAA ATATACATCA TAAAAGTACC AAAATAATTA  2158
                         *********** ********** ********** ********** **********
AI462015              7 : TGTAAAAAATC TGTTTAATAA ATATACATCT TAGAAGTACC AAAATAATTA    56

2159 : CTAAC--AAT ACATTATGTA CATCATTTAC AGGAGGGTAA C            2121
                         * ***  *** ********** ** ******* *  *       *
                     57 : CCAACAAAAT ACAACATATA CAACATTTAC A--AG----A A              91

Matching = 75/85 (88%)
```

FIG. 25D

```
         -98,365 K  -98,364,500  -98,364 K  -98,363,500  -98,363 K  -98,362,500  -98,362 K  -98,361,500  -98,361 K  -98,360,500
Genes
XP_002805065.1                                              NFKBIA                         1506  2001
XM_001067642.2                                                                                    XP_001067842.1

Rhesus monkey Nfkbia  1995 : TGGAAAAATC TGTTTAATAA ATATACATAA TAAAAGTACC AAAATAATTA  1944
                            ** ******* ********** ********** ********** **********
AI462015                 7 : TGTAAAAAATC TGTTTAATAA ATATACATCT TAGAAGTACC AAAATAATTA    56

1945 : CCAAC--AAT ACACTATGTA CACCATTTAC AGAAGGGTAA C            1907
                            * ***  *** ********** ** ******* ***        *
                        57 : CCAACAAAAT ACAACATATA CAACATTTAC --AAG----A A              91

Matching = 74/85 (87%)
```

METHOD FOR ESTABLISHING MODIFIED HOST CELL

CROSS-REFERENCE TO RELATED APPLICATIONS

This application is a National Stage application of PCT/JP2013/077629, filed Oct. 10, 2013, which claims priority from Japanese application JP 2012-225537, filed Oct. 10, 2012.

SEQUENCE LISTING

The instant application contains a Sequence Listing which has been submitted electronically in ASCII format and is hereby incorporated by reference in its entirety. Said ASCII copy, created on Mar. 6, 2017, is named 060641-0133_SL.txt and is 17,530 bytes in size.

TECHNICAL FIELD

The present invention relates to the production of recombinant proteins using cultured animal cells. More specifically, the present invention relates to a technique of establishing host cells capable of efficiently producing proteins of interest.

BACKGROUND ART

In the production of pharmaceutically useful proteins by gene recombination technology, use of animal cells permits complicated posttranslational modification and folding, which cannot be attained using prokaryotic cells. The animal cells have therefore been frequently used as host cells for recombinant protein production.

In recent years, a large number of biotechnology-based pharmaceuticals such as antibodies and biologically active proteins have been developed. Techniques of efficiently producing recombinant proteins in animal cells lead to the cost reduction of biotechnology-based pharmaceuticals and promise their stable supply to patients.

Thus, there has been a demand for methods for producing proteins with higher production efficiency.

A known technique of improving the production efficiency of a protein of interest involves transferring a gene of the protein of interest as well as an additional structural gene to host cells so that the gene is expressed at a high expression level.

For example, there is disclosed a method for producing a protein, comprising culturing cells which highly express a gene of a membrane transport protein taurine transporter (TauT) and which a DNA encoding a desired protein is transferred to (Patent Literature 1: WO2007/119774, Patent Literature 2: WO2009/051109).

According to another disclosure, the yield of a desired protein is increased by use of cells which a gene of cysteine sulfinic acid decarboxylase (CSAD), an enzyme of the taurine synthesis pathway, is transferred to (Patent Literature 3: WO2008/114673).

According to a further disclosure, the yield of a desired protein is increased by use of cells which an alanine aminotransferase (ALT) gene is transferred to (Patent Literature 4: WO2009/020144). The alanine aminotransferase, an enzyme that catalyzes the formation of glutamate from alanine, is also known as an enzyme glutamic pyruvic transaminase (GPT) contained in human liver cells.

According to a further disclosure, the yield of a desired protein is increased by use of cells which a gene of an anion exchanger (AE) having bicarbonate transporter functions is transferred to (Patent Literature 5: WO2009/054433).

These disclosures also show that the yield of the desired protein is further increased as a result of co-expressing CSAD and TauT, co-expressing ALT and TauT, co-expressing bicarbonate transporter and CSAD, or co-expressing bicarbonate transporter and ALT (Patent Literatures 3 to 5).

In previous studies, the present inventors have often failed to establish a cell line highly co-expressing 2 types of foreign genes stably by the transfer of these 2 types of foreign genes to host cells, even if a cell line stably expressing each gene can be established by the transfer of this gene alone. In this case, empirically, a cell line highly co-expressing 2 types of gene stably cannot be established, when the expression level of a gene identical to at least one of the foreign genes, or a counterpart gene in host cells is equal to or lower than the detection limit in Quantitative PCR (qPCR). Particularly, it has been impossible to establish host cells highly co-expressing genes of proteins having the same functions or genes of enzymes involved in the same metabolic reaction, for example, host cells highly co-expressing 2 types of membrane transport proteins or host cells highly co-expressing 2 types of enzymes. Alternatively, 2 types of sugar chain-related enzyme genes from GlycArt Biotechnology AG are expressed in host cells. In some cases, however, the afucosyl contents of antibodies in antibody-producing cells derived from host cells having higher expression levels of these enzymes have been confirmed to fall outside an expected range due to the unstable gene expression of the enzymes.

As mentioned above, two or more different genes are often difficult to highly express.

CITATION LIST

Patent Literature

Patent Literature 1: WO2007/119774
Patent Literature 2: WO2009/051109
Patent Literature 3: WO2008/114673
Patent Literature 4: WO2009/020144
Patent Literature 5: WO2009/054433

SUMMARY OF INVENTION

Technical Problem

The present invention provides a novel technique for stably overexpressing genes that are difficult to express in host cells for use in recombinant protein production. The present invention also provides a technique of establishing a cell line that grows stably with a short doubling time.

Solution to Problem

The research group of the present inventors has previously found a particular nucleic acid sequence that is a protein-non-coding nucleic acid sequence and is expressed as an RNA within host cells to thereby functionally control the expression of NfkBia (nuclear factor κB inhibitor α or I-κB (inhibitor-κB)) and improve the ability to produce recombinant proteins such as recombinant antibodies (PCT/JP2012/058577 (WO2012/137683)). The present inventors have collectively designated RNAs and DNAs having such functions and their sequences as APES (antibody production enhancing sequence) (also referred to as PPES (polypeptide production enhancing sequence)).

APES has been considered as a functional nucleic acid that activates NF-κ (kappa) B via the suppression of NfkBia (or I-κB) expression. Also, KSHV miRNA-K1 or the like is known as a nucleic acid having such functions (Lei, Xiufen et al., Nat. Cell. Biol., 12 (2), p. 193-199, 2010).

This time, the present inventors have found novel use of APES.

Specifically, the present inventors have found that APES works to cause the stable and high expression of transgenes so as to achieve (1) the construction of cells highly expressing a particular gene that is difficult to express in ordinary cells and (2) the construction of cells highly expressing stably two or more different genes, which are difficult to establish from ordinary cells.

Thus, the present application provides a method for highly expressing stably difficult-to-express foreign genes or foreign genes with unstable expression within a host cell by the transfer of the APES gene to the host cell.

The present application also provides a method for establishing a cell that grows stably with a short doubling time by the transfer of the APES gene to a host cell.

The APES gene is a DNA encoding a non-coding RNA (RNA that is not translated into a protein) suppressing the expression of NfkBia.

The present invention is summarized as follows:

(1) A method for establishing a cell line for recombinant protein production capable of stably expressing two or more foreign genes, comprising transferring a gene of a non-coding RNA suppressing the expression of NfkBia to a cell so that the gene is expressed.

(2) The method according to (1), wherein the two or more foreign genes encode proteins that are difficult to express stably at the same time.

(3) The method according to (2), wherein all of the proteins that are difficult to express stably at the same time belong to proteins having similar functions.

(4) The method according to (3), wherein the proteins having similar functions are transporters or metabolic enzymes.

(5) The method according to any of (1) to (4), wherein genes of two or more transporters (e.g., TauT and AE1) are transferred to the cell.

(6) The method according to any of (1) to (4), wherein genes of two or more metabolic enzymes (e.g., enzymes ALT1 and PC of the pyruvate metabolism pathway) are transferred to the cell.

(7) The method according to any of (1) to (4), wherein genes of TauT and two metabolic enzymes are transferred to the cell.

(8) A method for constructing a cell with a short doubling time, comprising transferring a DNA construct comprising a gene of a non-coding RNA suppressing the expression of NfkBia to a cell so that the non-coding RNA is expressed within the cell.

(9) A cell in which a gene of a non-coding RNA suppressing the expression of NfkBia is expressed by the transfer of the gene to the cell while two or more foreign genes are stably expressed.

(10) The method according to any of (1) to (8) or the cell according to (9), wherein the non-coding RNA suppressing the expression of NfkBia is a small RNA up to 30 bases long comprising a consecutive sequence of 19 to 25 bases in length, the small RNA being capable of binding to a portion of NfkBia mRNA by base pairing.

(11) The method according to any of (1) to (8) or the cell according to (9), wherein the non-coding RNA suppressing the expression of NfkBia is an mRNA-type non-coding RNA up to 561 bases long comprising a consecutive sequence of 19 to 25 bases in length, the mRNA-type non-coding RNA being capable of binding to a portion of NfkBia mRNA by base pairing.

(12) The method according to any of (1) to (8) or the cell according to (9), wherein the non-coding RNA suppressing the expression of NfkBia is an mRNA-type non-coding RNA 561 to 1579 bases long comprising a consecutive sequence of 19 to 25 bases in length, the mRNA-type non-coding RNA being capable of binding to a portion of NfkBia mRNA by base pairing.

(13) The method or the cell according to any of (10) to (12), wherein the consecutive sequence of 19 to 25 bases in length is an arbitrary partial sequence in the nucleotide sequence represented by SEQ ID NO: 2, or a complementary sequence thereof.

(14) The method according to any of (1) to (8) or the cell according to (9), wherein the gene of a non-coding RNA suppressing the expression of NfkBia has a nucleotide sequence represented by any of SEQ ID NOs: 1 to 16 and 29.

(15) The method according to any of (1) to (8) or the cell according to (9), wherein the gene of a non-coding RNA suppressing the expression of NfkBia is a DNA having the following nucleotide sequence or a complementary sequence thereof:

(a) a sequence capable of binding to a nucleotide sequence represented by any of SEQ ID NOs: 1 to 16 and 29 by base pairing;

(b) a nucleotide sequence identical to a nucleotide sequence represented by any of SEQ ID NOs: 1 to 16 and 29 except for 1 or several bases;

(c) a partial sequence of the 3'-untranslated region of the NfkBia gene, comprising a nucleotide sequence represented by any of SEQ ID NOs: 1 to 16 and 29; or (d) a nucleotide sequence identical to the sequence (c) except for 1 or several bases.

(16) The method according to any of (1) to (8) or the cell according to (9), wherein a gene of a desired protein is further transferred to the cell.

(17) The method or the cell according to (16), wherein the desired protein is an antibody.

(18) The method for establishing a cell line for recombinant protein production capable of stably expressing two or more foreign genes according to (1), wherein the method comprises:

transferring a first foreign gene and the gene of a non-coding RNA suppressing the expression of NfkBia to the cell so that these genes are expressed; and transferring a second foreign gene that is difficult to express stably at the same time with the first foreign gene, to the cell, wherein the first and second foreign genes are protein-encoding genes, and the established cell line for recombinant protein production expresses the gene of a non-coding RNA suppressing the expression of NfkBia, and the protein-encoding first and second foreign genes.

(19) The method for establishing a cell line for recombinant protein production capable of stably expressing two or more foreign genes according to (1), wherein the method comprises:

transferring a first foreign gene and the gene of a non-coding RNA suppressing the expression of NfkBia to the cell so that these genes are expressed;

transferring a second foreign gene to the cell; and
transferring a third foreign gene that is difficult to express stably at the same time with the second foreign gene, to the cell, wherein
the first, second, and third foreign genes are protein-encoding genes, and
the established cell line for recombinant protein production expresses the gene of a non-coding RNA suppressing the expression of NfkBia, and the protein-encoding first, second, and third foreign genes.
(20) The method according to (18) or (19), wherein the first foreign gene is a taurine transporter (TAUT) gene.
(21) The method according to any of (18) to (20), wherein a gene of a desired protein is further transferred to the cell to establish a host cell line for the production of the desired protein.

Advantageous Effects of Invention

The present invention has enabled various foreign genes to be stably overexpressed in host cells. Thus, a polypeptide that is difficult to express in ordinary cells can be produced as a medicament by use of the present invention. In addition, the present invention enhances the expression level of a difficult-to-express antigenic protein and thus facilitates developing an antibody against such an antigen. Moreover, the present invention permits construction of a cell highly expressing a plurality of genes stably and therefore enables a host cell for recombinant protein production incorporating a large number of useful genes to be prepared.

According to another aspect of the present invention, a cell that grows stably with a short doubling time can be established. Thus, use of such a cell as a host in recombinant protein production using cultured animal cells can achieve efficient production of proteins of interest.

BRIEF DESCRIPTION OF DRAWINGS

FIG. 12 shows a probe set used in the quantification of NfkBia expression (Reference Example 4).

FIG. 14 shows eight NfkB-binding sites (underlined) on mouse MCMV IE2 promoter (SEQ ID NO: 23) (Reference Example 4).

FIG. 15 discloses SEQ ID NOS 46, 46-47, 46, 48, 48 and 48, respectively, in order of appearance.

FIG. 18 shows results of shaker fed-batch culture, showing the effects on higher cell proliferation and on higher mAb-production brought about by the overexpression of APES (Reference Example 6).

FIG. 24 shows that a homologous sequence of AI462015 resides on the CHO-K1 cell genome (Reference Example 1). FIG. 24 discloses SEQ ID NOS 40 and 26, respectively, in order of appearance.

FIG. 25a shows that a partial sequence (nucleotides 7 to 91 from the 5' end) of AI462015 is conserved regardless of species (Reference Example 1). FIG. 25b shows that a partial sequence (nucleotides 7 to 91 from the 5' end) of AI462015 is conserved regardless of species (Reference Example 1). FIG. 25a discloses SEQ ID NOS 41 and 29, respectively, in order of appearance. FIG. 25b discloses SEQ ID NOS 42 and 29, respectively, in order of appearance.

FIG. 25c shows that a partial sequence (nucleotides 7 to 91 from the 5' end) of AI462015 is conserved regardless of species (Reference Example 1). FIG. 25*d* shows that a partial sequence (nucleotides 7 to 91 from the 5' end) of AI462015 is conserved regardless of species (Reference Example 1). FIG. 25*c* discloses SEQ ID NOS 43 and 29, respectively, in order of appearance. FIG. 25*d* discloses SEQ ID NOS 44 and 29, respectively, in order of appearance.

FIG. 25*e* discloses SEQ ID NOS 45 and 29, respectively, in order of appearance.

DESCRIPTION OF EMBODIMENTS

Figure 1:
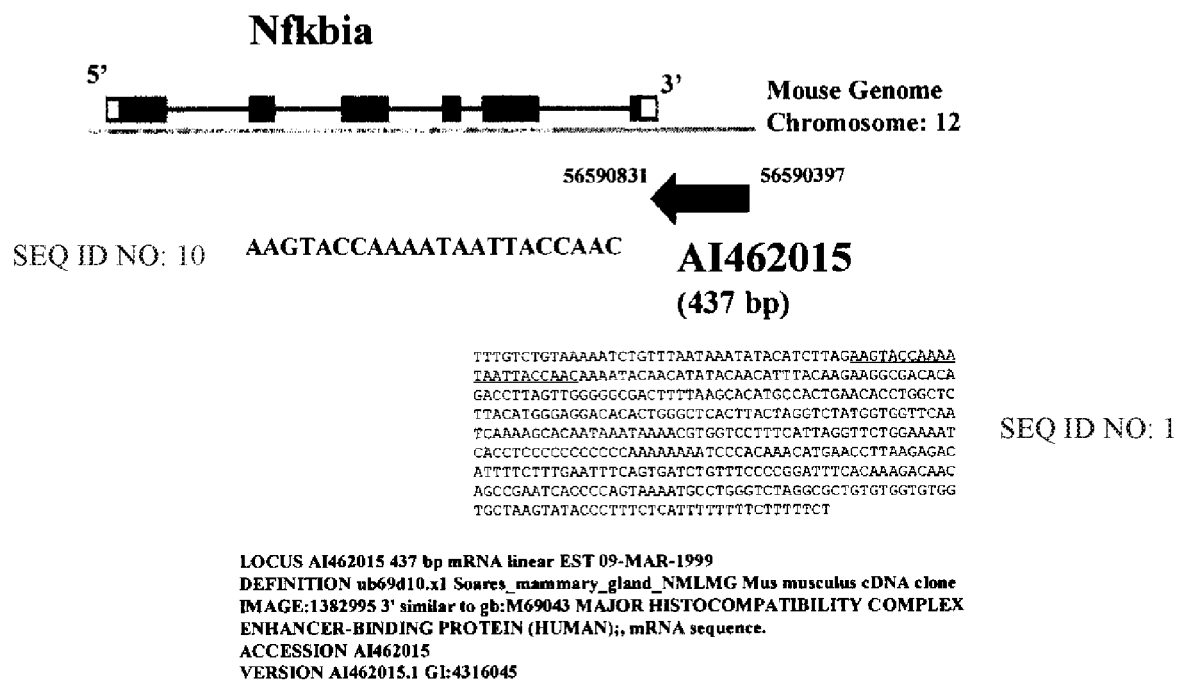
FIG. 1 shows the sequence of an identified AI462015 transcript and its position on the mouse genome (Reference Example 1).

Hereinafter, the embodiments of the present invention will be described in more detail.

(1) APES (Antibody Production Enhancing Sequence)

APES is a nucleic acid molecule that inactivates I-κB, an inhibitor protein of NF-κB, and is more specifically a nucleic acid molecule that suppresses the gene expression of an I-κB control subunit I-κBα (NfkBia). Such a nucleic acid molecule is composed principally of a non-coding RNA suppressing the expression of NfkBia. APES is a generic name for the non-coding RNA itself, a DNA encoding the RNA, and their sequences.

Alternatively, APES is a nucleic acid molecule comprising a nucleotide sequence capable of binding to a human-, mouse-, rat-, or hamster-derived NfkBia gene (DNA or mRNA) by base pairing and thereby suppressing the expression of NfkBia. Such a nucleic acid molecule is probably capable of binding to the NfkBia gene (DNA or mRNA) and thereby inhibiting the expression thereof. APES is a molecule that causes, for example, the RNA interference of NfkBia mRNA.

Alternatively, APES may be a double-stranded RNA (dsRNA), a siRNA, which is a short dsRNA, a siRNA dissociated into single strands, a shRNA, an antisense DNA or RNA, a microRNA (miRNA), or a mRNA-type non-coding RNA, comprising a sequence capable of binding to a human-, mouse-, rat-, or hamster-derived NfkBia gene (DNA or mRNA) by base pairing.

Alternatively, APES is a nucleic acid molecule comprising a nucleotide sequence that consists of a complementary sequence of the human-, mouse-, rat-, or hamster-derived NfkBia gene (DNA or mRNA) or comprises a partial sequence of this complementary sequence and is capable of suppressing the expression of NfkBia.

Alternatively, APES is a nucleic acid molecule comprising a nucleotide sequence that is a partial sequence of the human-, mouse-, rat-, or hamster-derived NfkBia gene (DNA or mRNA) or a complementary sequence of this partial sequence and is capable of suppressing the expression of NfkBia.

APES can be, for example, an oligonucleotide consisting of a sequence comprising a sequence homologous or complementary to a portion of the target NfkBia mRNA. Examples of such oligonucleotides include small RNAs having a sequence corresponding to 19 to 25 bases in the complementary strand of NfkBia mRNA or a sequence identical to the sequence except for one base and having the effect of suppressing the expression of NfkBia. In this context, the small RNA means a small non-coding RNA (snRNA). The snRNA includes miRNAs.

Alternatively, APES may be a long-chain mRNA-type non-coding RNA. Such a mRNA-type non-coding RNA can consist of, for example, a sequence up to 561 nucleotides long (561 mer) comprising a sequence capable of binding to the NfkBia gene (DNA or mRNA) by base pairing and have the effect of suppressing the expression of NfkBia. Alternatively, APES may be an mRNA-type non-coding RNA having a longer chain (hundreds to hundreds of thousands of nucleotide). For example, APES can be a nucleic acid molecule or sequence 200 to 100000 nucleotides long or 300 to 300000 nucleotides long. APES may be an mRNA-type non-coding RNA 561 to 1579 bases long or 500 to 1000 bases long comprising a sequence complementary (e.g., the snRNA sequence mentioned above) to a portion of NfkBia mRNA.

The sequence capable of binding by base pairing is not limited to a completely pairing sequence (i.e., a 100% complementary sequence), and the presence of non-pairing bases is also acceptable as long as these bases do not interfere with the functions. Alternatively, depending on the form of APES, partial complementation is rather preferred. Thus, for example, a sequence that is at least 70%, more preferably 80%, further preferably 90%, most preferably 95% homologous to the NfkBia gene (DNA or mRNA) containing an untranslated region, or a complementary sequence thereof is also included in the "sequence capable of binding by base pairing". For example, as for a 561 mer or 500 mer mRNA-type non-coding RNA, the at least 90% homologous sequence encompasses a mutant sequence that comprises 1 to 50 mismatched bases (or 1 to 56 mismatched nucleotides for the 561 mer RNA) resulting from base insertion, deletion, or point mutation and has the function of increasing the ability to produce a recombinant polypeptide such as a recombinant antibody in conjunction with the expression thereof in host cells or the function of suppressing the expression of NfkBia in conjunction with the expression thereof in host cells. Accordingly, for example, a sequence derived from an NfkBia orthologue (xenogeneic homologous gene) that has some degree of sequence similarity (e.g., 70% or higher homology) and is derived from an organism species different from a host cell may also be used as APES.

Alternatively, the sequence capable of binding by base pairing encompasses a sequence capable of binding to NfkBia mRNA under conditions such as intracellular conditions. Such a sequence includes, for example, a sequence that hybridizes under conditions known to those skilled in the art as highly stringent conditions and has desired functions. One example of the highly stringent conditions is the incubation of a polynucleotide and another polynucleotide at a hybridization temperature of 42° C. for 12 to 16 hours (wherein one of the polynucleotides may be attached to the surface of a solid such as a membrane) in a hybridization buffer solution containing 6×SSPE or SSC, 50% formamide, 5×Denhardt's reagent, 0.5% SDS, and 100 μg/ml of a fragmented denatured salmon sperm DNA, followed by several washings of the resulting hybrid with a wash buffer solution containing 1×SSC and 0.5% SDS at an optimal temperature of 42° C. or higher. For other specific conditions, see many experimental manuals well known to those skilled in the art, such as Sambrook et al., "Molecular Cloning: A Laboratory Manual, the 3rd Edition", Cold Spring Harbor Laboratory Pr; and Ausubel et al., "Current Protocols in Molecular Biology", Maruzen Co., Ltd.

According to another embodiment, APES is a nucleic acid molecule comprising a nucleotide sequence that is homologous or complementary to a partial sequence of the 3'-untranslated region of human-, mouse-, rat-, or hamster-derived NfkBia mRNA and is capable of suppressing the expression of NfkBia.

Figure 23:
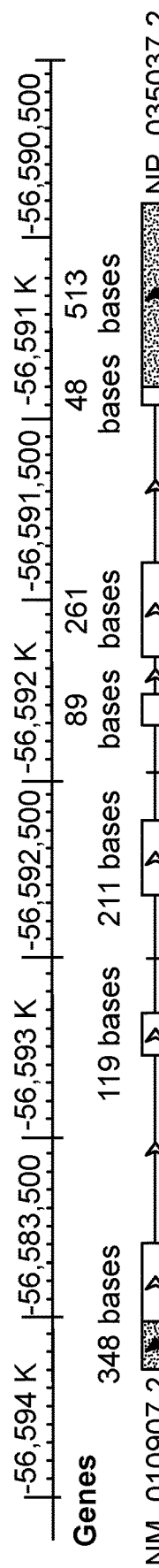
FIG. 23 shows that AI462015 is a complementary strand of mouse Nfkbia mRNA (Reference Example 1).

As described in Reference Examples mentioned later, the present inventors have found an mRNA-type non-coding RNA that exhibited an expression level increased in correlation with the ability of cultured CHO cells to produce antibodies. This RNA has been identified as a transcript of a known sequence (FIG. 1, GenBank Accession ID: AI462015, SEQ ID NO: 1) consisting of 437 bases in the mouse genome. FIG. 1 shows the sequence of this AI462015 and its position on the mouse genome. The 437-base transcript of AI462015 corresponds to a complementary strand of the 3'-untranslated region (513 bases) of mouse NfkBia mRNA (FIG. 23). The present inventors have further found that the yield of a desired polypeptide can be increased by the transfer of a nucleic acid molecule having a partial sequence derived from AI462015 to host cells.

The AI462015-derived sequence or partial sequence thereof mentioned above is conserved not only in rodents such as mice and hamsters but in humans and thus also considered as a highly conservative sequence for other mammals and other animals such as fish and insects. Thus, a partial sequence of the 3'-untranslated region of NfkBia mRNA derived from any of various animal cells adaptable to the AI462015-derived sequence or the partial sequence thereof, or a complementary sequence thereof can also be used as the APES sequence of the present invention.

As one specific example, APES has a mouse AI462015-derived partial sequence or a sequence derived from this partial sequence by the substitution, deletion, or addition of 1 or several bases. Particularly, examples thereof include: a 165-base DNA sequence consisting of a nucleotide sequence from G at nucleotide 4 to C at nucleotide 168 from the 5' end (SEQ ID NO: 2, APES165); a complementary (antisense) DNA sequence thereof; sequences comprising RNA sequences transcribed from these DNAs; and partial sequences of any length in these sequences. Alternative examples thereof include: a 434-base DNA sequence consisting of a nucleotide sequence from G at nucleotide 4 from the 5' end to T at the 3' end (SEQ ID NO: 3, APES434); a complementary (antisense) DNA sequence thereof; sequences comprising RNA sequences transcribed from these DNAs; and partial sequences of any length derived from these sequences. Such sequences also include: sequences comprising mammal (e.g., human, hamster, or rat)-derived sequences corresponding to the mouse AI462015 sequence; partial sequences thereof; and nucleotide sequences derived from these partial sequences by the substitution, deletion, or addition of 1 or several bases.

In one embodiment, APES has a nucleotide sequence from nucleotides 4 to 133 from the 5' end (SEQ ID NO: 4, APES130) in AI462015, or a partial sequence derived from this sequence. Examples thereof include a DNA sequence from nucleotides 4 to 68 from the 5' end (SEQ ID NO: 5, APES4-68) or nucleotides 69 to 133 from the 5' end (SEQ ID NO: 6, APES69-133), a complementary DNA sequence thereof, and sequences transcribed from these DNAs In one embodiment, APES has a 52-base sequence from nucleotides 40 to 91 from the 5' end (SEQ ID NO: 7) in AI462015, or a sequence derived from a partial sequence obtained by the cleavage of the 52-base sequence at an arbitrary position. Examples thereof include a DNA sequence of the former part (29 bases of APES40-68, 24 bases of APES40-63, or 22 bases of APES40-61) or the latter part (23 bases of APES69-91), a complementary DNA sequence thereof (corresponding to SEQ ID NOs: 8 to 11, respectively), and sequences transcribed from these DNAs.

The 52-base sequence mentioned above is identical to the complementary strand of the 3'-untranslated region of the rat NfkBia gene except for one base. Its 5'-sequence of 24 bases (APES40-63, SEQ ID NO: 9) is identical to the 3'-untranslated region of the human NfkBia gene. Its 5'-sequence of 22 bases (APES40-61, SEQ ID NO: 10: AAGTAC-CAAAATAATTACCAAC) is identical to the complementary strand of the 3'-untranslated region of NfkBia mRNA regardless of species such as rats, rhesus monkeys, dogs, and horses. The expression of a partial sequence complementary to the 3'-untranslated region of the NfkBia gene in host cells is expected to produce an RNAi effect. For example, an RNA having a sequence complementary to 19 to 25 bases of the aforementioned 52-base sequence may act as a microRNA (miRNA) on the untranslated region of NfkBia mRNA to thereby inhibit the translation.

Alternatively, APES has an 85-base sequence from nucleotides 7 to 91 from the 5' end (SEQ ID NO: 29) in AI462015, or a sequence derived from a partial sequence obtained by the cleavage of the 85-base sequence at an arbitrary position. An RNA having a sequence complementary to 19 to 25 bases of the aforementioned 85-base sequence may act as a microRNA (miRNA) on the untranslated region of NfkBia mRNA to thereby inhibit the translation.

In one embodiment, APES has a sequence that is found by search for a 21-base siRNA. Such a sequence is, for example, a miRNA sequence comprising a sequence complementary to a DNA sequence from nucleotides 84 to 104 (SEQ ID NO: 12, APES84-104), nucleotides 99 to 119 (SEQ ID NO: 13, APES99-119), or nucleotides 101 to 121 (SEQ ID NO: 14, APES101-121) in AI462015. Since the sequence from nucleotides 71 to 112 (SEQ ID NO: 16) in APES69-133 mentioned above is a region that has been quantified on GENECHIP® and is actually expressed at a high level, APES84-104 is likely to function as a miRNA.

In another embodiment, APES may be a known non-coding RNA suppressing the expression of NfkBia. Examples of such nucleic acid molecules include KSHV (Kaposi's sarcoma-associated herpesvirus) miRNA-K1 (for its sequence information, see, for example, X Cai et al., Proc Natl Acad Sci USA. 2005 Apr. 12; 102 (15): 5570-5575).

Also, a novel nucleic acid molecule having APES activity may be chemically synthesized or isolated from an organism source on the basis of the structural or functional feature of APES. The structural feature of APES is that APES is a nucleic acid molecule comprising a sequence complementary to a portion of the target NfkBia mRNA. The nucleic acid molecule may be in any form and may be a DNA, a DNA transcript, an mRNA, a cDNA, an exosome RNA, a chemically synthesized single-stranded RNA, a chemically synthesized double-stranded RNA, or the like. The functional feature is that the ability to produce a recombinant polypeptide such as a recombinant antibody is increased in conjunction with the expression thereof in host cells or that the expression of NfkBia is suppressed in conjunction with the expression thereof in host cells.

For the isolation of APES from an organism source, this APES can be derived from any organism without particular limitations. Specific examples thereof include APES derived from animals including: primates such as humans and chimpanzees; rodents such as mice, rats, and hamsters; livestock such as cattle, pigs, and goats; birds such as chickens; fish such as zebrafish; insects such as flies; and nematodes. APES is preferably derived from a human, a rodent, or an animal of the same species as a host cell. For example, when a strongly APES-expressing cell is a Chinese hamster ovary cell (CHO cell), human-, mouse-, or hamster-derived APES is preferred.

Such a nucleic acid molecule can be prepared by a method known to those skilled in the art. For example, the nucleic acid molecule may be prepared by: preparing total RNA from cultured cells highly producing a recombinant polypeptide such as a recombinant antibody; synthesizing an oligonucleotide on the basis of the nucleic acid sequence of the present invention (e.g., APES165 of SEQ ID NO: 2); and amplifying cDNA having the features of APES through PCR reaction using the oligonucleotide as a primer. After preparation of a small RNA from cultured cells highly producing a recombinant polypeptide such as a recombinant antibody, a cDNA library can be prepared to obtain a small RNA comprising a partial sequence complementary to NfkBia mRNA on the basis of the nucleotide sequence of the cloned cDNA. The cDNA library may be constructed by a method described in, for example, Sambrook, J. et al., Molecular Cloning, Cold Spring Harbor Laboratory Press (1989), after preparation of a small RNA such as a microRNA (miRNA).

Also, the genomic DNA for APES expression can be isolated by the sequencing of the obtained cDNA and the screening of a genomic DNA library using the obtained cDNA as a probe.

Specifically, the following procedures may be carried out: first, total RNA is isolated from cells, tissues, or the like that are likely to express the APES of the present invention. For the isolation of mRNA, total RNA is prepared by a known method, for example, a guanidine ultracentrifugation method (Chirgwin, J. M. et al., Biochemistry (1979) 18, 5294-5299) or an AGPC method (Chomczynski, P. and Sacchi, N., Anal. Biochem. (1987) 162, 156-159) and then further purified using RNEASY® Mini Kit (Qiagen N.V.) or the like.

cDNA is synthesized from the obtained total RNA using reverse transcriptase. The cDNA synthesis may be carried out using SUPERSCRIPT™ II Reverse Transcriptase (Invitrogen Corp.) or the like. Also, the cDNA can be synthesized and amplified according to a 5'-RACE method (Frohman, M. A. et al., Proc. Natl. Acad. Sci. U.S.A. (1988) 85, 8998-9002; and Belyaysky, A. et al., Nucleic Acids Res. (1989) 17, 2919-2932) using 5'-AMPLIFINDER" RACE Kit (manufactured by Clontech Laboratories, Inc.) and polymerase chain reaction (PCR) with primers or the like.

The DNA fragment of interest is prepared from the obtained PCR product and ligated to a vector DNA. The recombinant vector thus prepared is transferred to *E. coli* or the like. Colonies are selected to prepare a desired recombinant vector. The nucleotide sequence of the DNA of interest can be confirmed by a known method, for example, a dideoxynucleotide chain termination method.

The obtained DNA can also be modified using a commercially available kit or a known method. Examples of the modification include the introduction of single-nucleotide mutation by site-directed mutagenesis. The sequence thus modified is also included in the scope of the present invention as long as the modified sequence has APES activity. In this context, the phrase "having APES activity" refers to having the function of suppressing the expression of NfkBia (I-κBα) through expression within host cells.

In the present specification, the nucleic acid molecule having APES activity is also referred to as the nucleic acid molecule of the present invention.

(2) Transfer of APES to Host Cell and its Expression

The present invention involves transferring APES, i.e., a gene of a non-coding RNA suppressing the expression of NfkBia, to a host cell and further involves expressing APES, preferably, strongly expressing APES.

The strong expression of APES means increase in the expression level of APES compared with an original cell. Examples of the original cell can include, but are not particularly limited to, cells, such as CHO cells, which are used as hosts in recombinant protein production. Referring to Reference Examples mentioned later, as a specific example, the original cell has an AI462015 signal value of 2000 or less before antibody gene transfer in a GENECHIP® experiment using an oligonucleotide array from Affymetrix, Inc. (Affymetrix MOUSE430_2). By contrast, the increase in the expression level of APES means that, for example, the signal value of AI462015 is twice or more that of the original cell.

The cell strongly expressing APES by the transfer of the APES gene comprises endogenous or exogenous APES within the cell. Examples of the strongly APES-expressing cell include cells which APES is artificially transferred to.

The cells which APES is artificially transferred to can be prepared by a method known to those skilled in the art. For example, the cells can be prepared by the incorporation of an APES-encoding DNA sequence into a vector, with which cells are then transformed.

In the present specification, the cells which APES is artificially transferred to also encompass cells strongly expressing APES as a result of activating endogenous APES by gene activation technology (see, for example, International Publication No. WO94/12650).

A typical example of the endogenous APES is APES as a DNA sequence encoded on the genome of a host cell. The cell according to the present invention is not limited to the cells based on the gene activation technology, and, for example, cells strongly expressing APES by the transcriptional activation of endogenous APES due to some factor after antibody gene transfer may also be used in the present invention.

(3) Expression Vector

The expression vector is useful for the strong expression of APES by a host cell and for the expression of foreign polypeptides such as transporters or metabolic enzymes. The expression vector is also used for the expression of foreign polypeptides useful as pharmaceutical active ingredients or antigens.

Examples of the expression vector that may be used in the present invention include mammal-derived expression vectors (e.g., pcDNA3 (manufactured by Invitrogen Corp.), pEGF-BOS (Nucleic Acids Res 1990, 18 (17), p5322), pEF, and pCDM8), insect cell-derived expression vectors (e.g., "BAC-TO-BAC® baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIpneo), yeast-derived expression vectors (e.g., "Pichia Expression Kit" (manufactured by Invitrogen Corp.), pNV11, and SP-Q01), and *Bacillus subtilis*-derived expression vectors (e.g., pPL608 and pKTH50).

The expression vector for the expression of a foreign polypeptide comprises a DNA encoding the polypeptide and an expression control sequence capable of promoting the expression of the DNA. Likewise, the expression vector for the expression of APES comprises a DNA encoding APES and an expression control sequence capable of promoting the expression of the DNA. A single vector may be constructed such that one or more polypeptides and APES are expressed. In the case of activating, for example, the APES or polypeptide gene as a portion of the host genome by use of gene activation technology, an expression control sequence that promotes the expression of such a host cell-derived DNA may be transferred to the host cell.

Examples of the expression control sequence include an appropriate promoter, enhancer, transcription terminator, a Kozak sequence containing a start codon (i.e., ATG) in a protein-encoding gene, a splicing signal for intron, a polyadenylation site, and a stop codon. The vector can be appropriately constructed by those skilled in the art.

The expression control sequence preferably contains a promoter/enhancer region capable of increasing gene transcription levels in the animal cell used. The promoter/enhancer region involved in the expression of a gene encoding a desired polypeptide may or may not contain a NF-κB-binding sequence.

For the purpose of expression in mammalian cells such as CHO cells, COS cells or NIH3T3 cells, the vector preferably has a promoter necessary for expression within the cells, for example, SV40 promoter (Mulligan et al., Nature (1979) 277, 108), MMLV-LTR promoter, EF1α promoter (Mizushima et al., Nucleic Acids Res. (1990) 18, 5322), or CMV promoter. More preferably, the vector also has a gene for the selection of transformants (e.g., a drug resistance gene that permits discrimination using a drug (neomycin, G418, etc.)). Examples of the vector having such properties include pMAM, pDR2, pBK-RSV, pBK-CMV, pOPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having an SV40 T antigen gene on their chromosomes to transform the cells with vectors having a replication origin of SV40 (pcD, etc.). Also, a replication origin derived from polyomavirus, adenovirus, bovine papillomavirus (BPV), or the like may be used. The expression vectors for increasing the number of gene copies in the host cell system can additionally contain a selection marker such as an aminoglycoside phosphoryl transferase (APH) gene, a thymidine kinase (TK) gene, an *E. coli* xanthine guanine phosphoribosyltransferase (Ecogpt) gene, or a dihydrofolate reductase (dhfr) gene.

(4) Host Cell

The host cell used in the present invention is not particularly limited. The host cell may be any cell including eukaryotic cells (e.g., animal cells, plant cells, and yeasts) and prokaryotic cells (e.g., *E. coli* and *Bacillus subtilis*) and is preferably an animal cell derived from an insect, fish, an amphibian, a reptile, or a mammal, particularly preferably a mammalian cell. Examples of the origin of the mammalian cell include primates such as humans and chimpanzees, rodents such as mice, rats, and hamsters, and other mammals. A human or a rodent is preferred. The cell of the present invention is further preferably a cultured mammalian cell, such as a CHO, COS, 3T3, myeloma, BHK, HeLa, or Vero cell, which is often used in ordinary polypeptide expression.

CHO cells are particularly preferred for the purpose of large-scale expression of a polypeptide useful as a medicament or an antigen. In particular, DHFR gene-deficient CHO cells dhfr-CHO (Proc. Natl. Acad. Sci. USA (1980) 77, 4216-4220) or CHO K-1 (Proc. Natl. Acad. Sci. USA (1968) 60, 1275) can be preferably used as CHO cells.

The CHO cells mentioned above are preferably a DG44 line, a DXB-11 line, K-1, or CHO-S, particularly preferably a DG44 line or a DXB-11 line.

The host cell can be used as, for example, a production system for the manufacture of a desired polypeptide such as a medicament or an antigen. Such a cell may be a natural cell capable of producing the desired polypeptide or may be a cell which a DNA encoding the desired polypeptide is transferred to. A transformed cell which a DNA encoding the desired polypeptide is transferred to is preferred.

As an example, the transformed cell which a DNA encoding the desired polypeptide is transferred to is a host cell transfected with an expression vector comprising at least the DNA encoding the desired polypeptide.

In the present invention, the cell "which a DNA (or a gene) is transferred to" encompasses cells transfected with an exogenous DNA as well as cells in which an endogenous DNA has been activated by gene activation technology (see, for example, International Publication No. WO94/12650), resulting in the initiation or increase of the expression of a protein corresponding to the DNA or the transcription of the DNA.

In the case of producing the desired polypeptide using the cells which APES is artificially transferred to, the order in which APES and a gene encoding the desired polypeptide are transferred is not particularly limited. After transfer of APES, the gene encoding the desired polypeptide may be transferred; or after transfer of the gene encoding the desired polypeptide, APES may be transferred. Alternatively, APES and the gene encoding the desired polypeptide may be transferred at the same time.

In the case of using the vector, APES and the gene encoding the desired polypeptide may be transferred at the same time via a single vector or may be separately transferred using a plurality of vectors.

(5) Foreign Gene

In the present invention, APES can be transferred to a host cell in advance and strongly expressed so that difficult-to-express foreign genes or foreign genes with unstable expression are highly expressed stably within the cell.

In the case of using the host cell in the production of a desired polypeptide, a gene of the desired polypeptide to be produced as well as other foreign genes can be transferred to the host cell and highly expressed stably within the cell.

Preferably, the yield of the desired polypeptide is increased by the expression of foreign genes within the transformed cell which a DNA encoding the desired polypeptide is transferred to. Examples of such foreign genes include DNAs encoding taurine transporter (TauT), cysteine sulfinic acid decarboxylase (CSAD), alanine aminotransferase (ALT), anion exchanger (AE), pyruvate carboxylase (PC), and X-box binding protein (XBP-1).

In the present invention, APES is transferred to the host cell in advance and strongly expressed therein. A plurality of foreign genes other than the gene of the desired protein can be transferred to the host cells and stably expressed therein. Preferably, the yield of the desired polypeptide is increased by the expression of the gene of the desired polypeptide as well as two or more other particular foreign genes in the host cell. As a result, a cell line suitable for recombinant protein production can be established.

Such two or more foreign genes can be genes encoding proteins that are difficult to express stably at the same time. Specifically, APES is transferred to the host cell in advance and overexpressed therein. Two or more foreign genes that are difficult to express stably at the same time, other than the gene of the desired polypeptide, can thereby be stably expressed at the same time. The phrase "difficult to express stably at the same time" denotes the combination of foreign genes encoding two or more proteins that are not stably expressed at the same time in a host cell without the transfer of APES.

In this context, the "two or more foreign genes that are difficult to express stably at the same time" refer to foreign genes that can be transferred each alone to an animal cell without the transfer of APES, preferably a host cell before transfer of the gene of the desired protein, to establish a cell line stably expressing each gene, but fail to yield a cell expressing the two or more protein-encoding foreign genes at the same time even by screening using an agent or the like after transfer of these two or more foreign genes. In this case, preferably, the expression level of a gene identical to at least one of the foreign genes, or a counterpart gene in the host cell before transfer of the foreign genes is equal to or lower than the detection limit in qPCR.

Even if the cell of the present invention is a host cell for the production of the desired protein in which two or more protein-encoding foreign genes have been successfully introduced, the expression level of at least one of the two or more protein-encoding foreign genes may be decreased to lower than 50%, preferably 30% or lower, more preferably 10% or lower, most preferably zero by screening for the gene amplification of the desired protein using at least two treatments with drugs such as MTX after transfer of the gene of the desired protein. In the present invention, such genes are referred to as the "two or more foreign genes that are difficult to express stably at the same time".

In another embodiment, the "two or more foreign genes that are difficult to express stably at the same time" refer to genes in which, when compared with the expression levels of the two or more protein-encoding foreign genes during screening of cells which the two or more protein-encoding foreign genes are transferred to but no APES is transferred to, the expression level of at least one of the two or more protein-encoding foreign genes is decreased to lower than 50%, preferably 30% or lower, more preferably 10% or lower, most preferably zero after at least 15-generation subculture of the cells.

When the cell of the present invention is a host cell for the production of the desired protein, the "stable expression at the same time" specifically means that after transfer of the gene of the desired protein to a host cell which two or more protein-encoding foreign genes are transferred to and contains APES, the expression levels of the two or more protein-encoding foreign genes are each kept at 50% or higher, preferably 70% or higher, even after screening for the gene amplification of the desired protein using at least two treatments with drugs such as MTX.

In another embodiment, the "stable expression at the same time" means that, when compared with the expression levels of the two or more foreign genes during screening of cells which the two or more foreign genes are transferred to, the expression levels of the two or more protein-encoding foreign genes are each kept at 50% or higher, preferably 70% higher, more preferably 80% or higher, even after at least 15-generation subculture of the cells.

In the present invention, the cell line in which the "stable expression at the same time" of the two or more foreign genes is maintained as mentioned above is referred to as an established cell line.

The "proteins that are difficult to express stably at the same time" according to the present invention can belong to proteins having similar functions. Examples of the combination of the proteins having similar functions that are difficult to express stably at the same time include the combination of two or more types of membrane transport proteins or accessory proteins necessary for the functions thereof, two or more types of enzyme proteins, preferably metabolic enzymes involved in the same metabolic pathway, or two or more types of transcription factors.

Alternatively, the combination of the proteins that are difficult to express stably at the same time may be the combination of two or more types of membrane transport proteins with one or two or more types of enzyme proteins. Alternatively, the combination of the proteins that are difficult to express stably at the same time may be the combination of one or two or more types of membrane transport proteins with two or more types of enzyme proteins.

The membrane transport proteins refer to proteins that reside in biomembranes and mediate the transport of materials. These proteins are also called transporters, carriers, permeases, etc. An important role of the cell membrane is the function of causing the selective permeation of various ions, nutrients, and the like. These membrane proteins are responsible for this function. The membrane transport proteins also include proteins that mediate the transport of organic materials such as sugars or amino acids, and ion pumps and ion channels, which are ion transporters. Various sugar or amino acid-transporting proteins (transporters and permeases) and ion transporters have been purified, and their genes are known.

In the present invention, genes of the proteins having similar functions can be, for example, the combination of two or more types of transporter genes. Examples of the 2 types of transporters include TauT and AE1.

A typical example of the enzyme proteins having similar functions is the combination of a plurality of metabolic enzymes. Genes of the enzyme proteins having similar functions can be, for example, two or more types of metabolic enzyme genes of the same pathway. Such metabolic enzymes may be two or more enzymes that promote continuous reactions in the same pathway. The metabolic enzymes of the same pathway can be, for example, enzymes that catalyze amino acid degradation reaction. The metabolic enzymes may be, for example, enzymes of the pyruvate metabolism pathway. Examples of the two or more enzymes of the pyruvate metabolism pathway can be ALT1 and PC.

Alternatively, the enzyme proteins having similar functions may be, for example, the combination of a plurality of glycosyltransferases.

The combination of one or two or more types of membrane transport proteins with two or more types of enzyme proteins can be, for example, TauT and two metabolic enzymes.

As mentioned above, the artificial expression of APES in a host cell can be achieved by the artificial transfer of the gene of a non-coding RNA suppressing the expression of NfkBia to a cell and the expression of the gene. Likewise, the expression of two or more foreign genes can also be achieved by the artificial transfer of these foreign genes to a cell and the expression of the genes.

An exogenous DNA (which may be incorporated in a vector) can be transferred to the host cell by a method, for example, a calcium phosphate method, a DEAE dextran method, a method using cationic ribosome DOTAP (manufactured by Boehringer Mannheim), electroporation, Nucleofection (Amaxa; currently, Lonza Group Ltd.), or lipofection.

In the present invention, the cell "which a DNA (or a gene) is transferred to" encompasses cells transfected with an exogenous DNA as well as cells in which an endogenous DNA has been activated by gene activation technology (see, for example, International Publication No. WO94/12650), resulting in the initiation or increase of the expression of a protein corresponding to the DNA or the transcription of the DNA.

For transferring two or more foreign protein genes that are difficult to express stably at the same time to the host cell and stably expressing these genes, it is preferred that APES should be transferred to the host cell in advance before transfer of the second foreign gene. In the case of using the vector, preferably, APES and second or later foreign genes are separately transferred using a plurality of vectors.

On the other hand, the order in which the first foreign gene and APES are transferred is not particularly limited. After transfer of APES, the first foreign gene may be transferred; or after transfer of the first foreign gene, APES may be transferred. Alternatively, APES and the first foreign gene may be transferred at the same time. In the case of using the vector, APES and the first foreign gene may be transferred at the same time via a single vector or may be separately transferred using a plurality of vectors.

(6) Cell Line for Recombinant Protein Production

In the present invention, a cell line for recombinant protein production highly expressing a plurality of protein-encoding foreign genes stably even after repetitions of subculture can be obtained by the transfer of the gene (APES) of a non-coding RNA suppressing the expression of NfkBia and the expression of the gene.

In addition, a cell line for recombinant protein production that can grow stably with a short doubling time can be obtained by the transfer of the APES gene to a host cell. Such a cell may be a cell highly expressing stably other transferred foreign genes in addition to APES.

As examples of the cell provided by the present invention, as shown in Examples mentioned later, APES165 (SEQ ID NO: 2: gtctgtaaaa atctgtttaa taaatataca tcttagaagt accaaaataa ttaccaacaa aatcaacat atacaacatt tacaagaagg cgacacagac cttagttggg ggcgactttt aagcacatgc cactgaacac ctggctctta catgggagga cacac) is first transferred to a highly TauT-expressing cell. To the cell thus established, subsequently, another transporter gene is further transferred to thereby establish a cell highly co-expressing two cooperatively functioning transporters stably. Also, APES165 is first transferred to a highly TauT-expressing cell. To the cell thus established, subsequently, genes of two enzymes of the pyruvate metabolism pathway are further transferred to thereby establish a cell highly co-expressing stably TauT and two enzymes that promote continuous reactions of the pyruvate metabolism pathway. These cells have properties preferred for recombinant protein production and as such, are suitable as host cells for the production of desired proteins useful as medicaments or antigens. These cells can be cultured as hosts after artificial transfer of genes of the desired proteins and allowed to produce the desired proteins. The produced proteins can be recovered to produce the desired proteins.

EXAMPLES

Hereinafter, the present invention will be described specifically with reference to Examples. However, these Examples are provided merely for illustrative purposes and are not intended to limit the scope of the present invention.

Example 1

Establishment of Cell Highly Expressing Particular Difficult-to-Express Genes (1) The membrane proteins TauT and AE1 function cooperatively through the entry and exit of chlorine ions on cell surface. In spite of previous repetitive attempts to establish host cells highly expressing TauT and AE1 at the same time in order to enhance the TauT functions of highly TauT-expressing cells, the deposition of floating cells was observed during the course of drug selection, and the establishment of co-expressing cells ended in failure. In this case, the original expression level of AE1 in the host cells was equal to or lower than the detection limit in qPCR.

(2) The enzymes ALT1 and pyruvate carboxylase (PC) catalyze the biosynthesis of pyruvate from alanine and oxaloacetate from the pyruvate. In spite of previous attempts to highly express PC in highly ALT1-expressing host cells in order to promote the reactions of the metabolic pathway leading to the TCA circuit, the establishment of co-expressing cells ended in failure. In this case, the original expression level of ALT1 in the host cells was equal to or lower than the detection limit in qPCR.

In these two cases, however, APES was highly expressed in advance before transfer of the second gene to thereby successfully establish cells highly expressing three or more types of genes including APES. Specifically, in the case of (1), TAUT/APES cells in which APES was highly expressed in highly TauT-expressing cells were constructed, and then, AE1 was transferred thereto to thereby establish highly proliferative TAUT/APES/AE1 cells highly expressing TauT and AE1. In the case of (2), TAUT/APES/ALT1 cells highly expressing ALT1 were constructed from the highly TAUT/APES-expressing cells of (1), and then, PC was transferred thereto to thereby establish highly proliferative TAUT/APES/ALT1/PC cells highly expressing ALT1 and PC. On the other hand, TAUT/ALT1/PC cells highly expressing ALT1 and PC were not established from TAUT/ALT1 cells without the high expression of APES.

In the present Examples, CHO cells of DXB-11 line were used as host cells.

Example 1-1

Establishment of DXB11/TAUT/APES Cell

Figure 26:
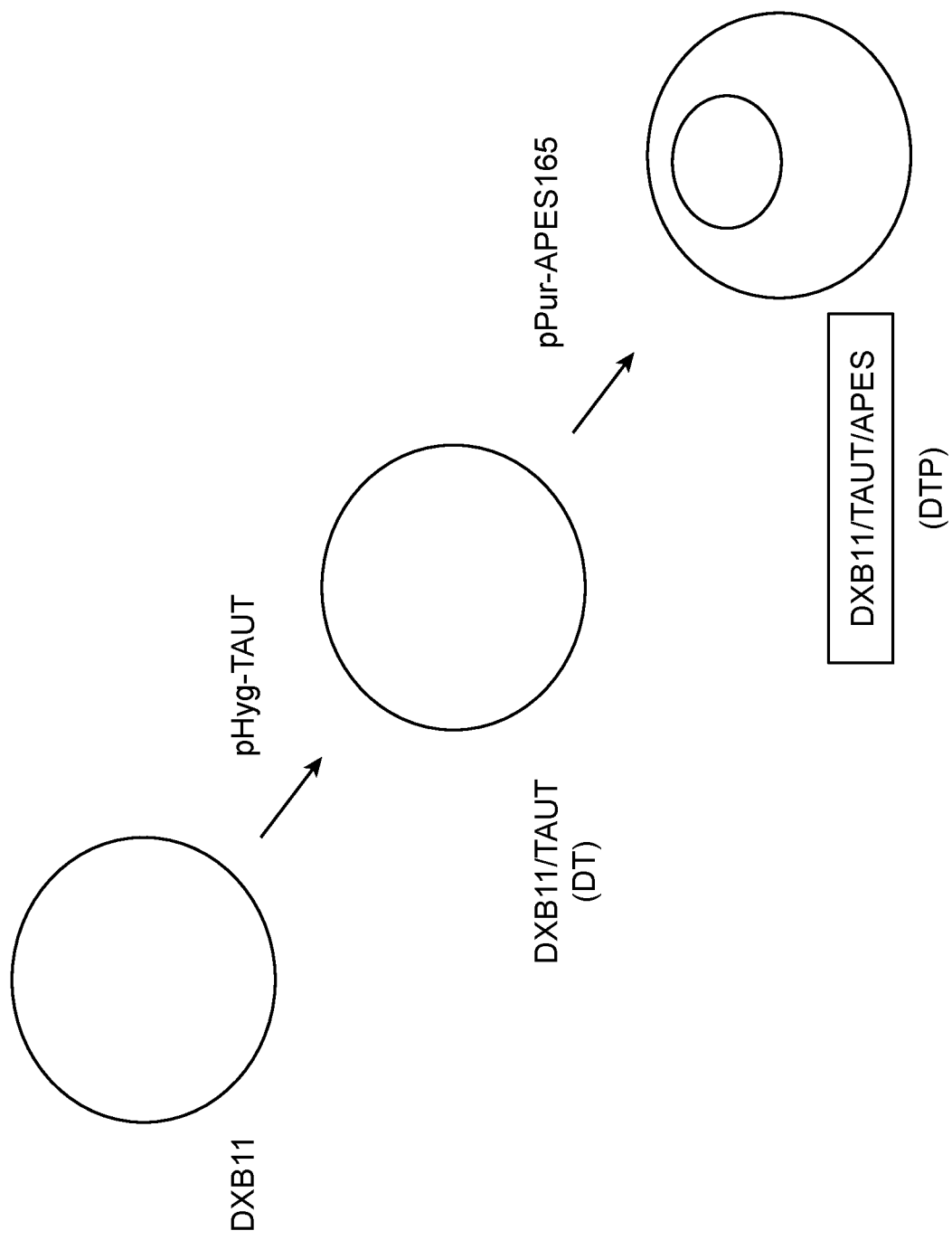
FIG. 26 shows the establishment of DXB11/TAUT/APES (DTP) host cells (Example 1).
Figure 27:
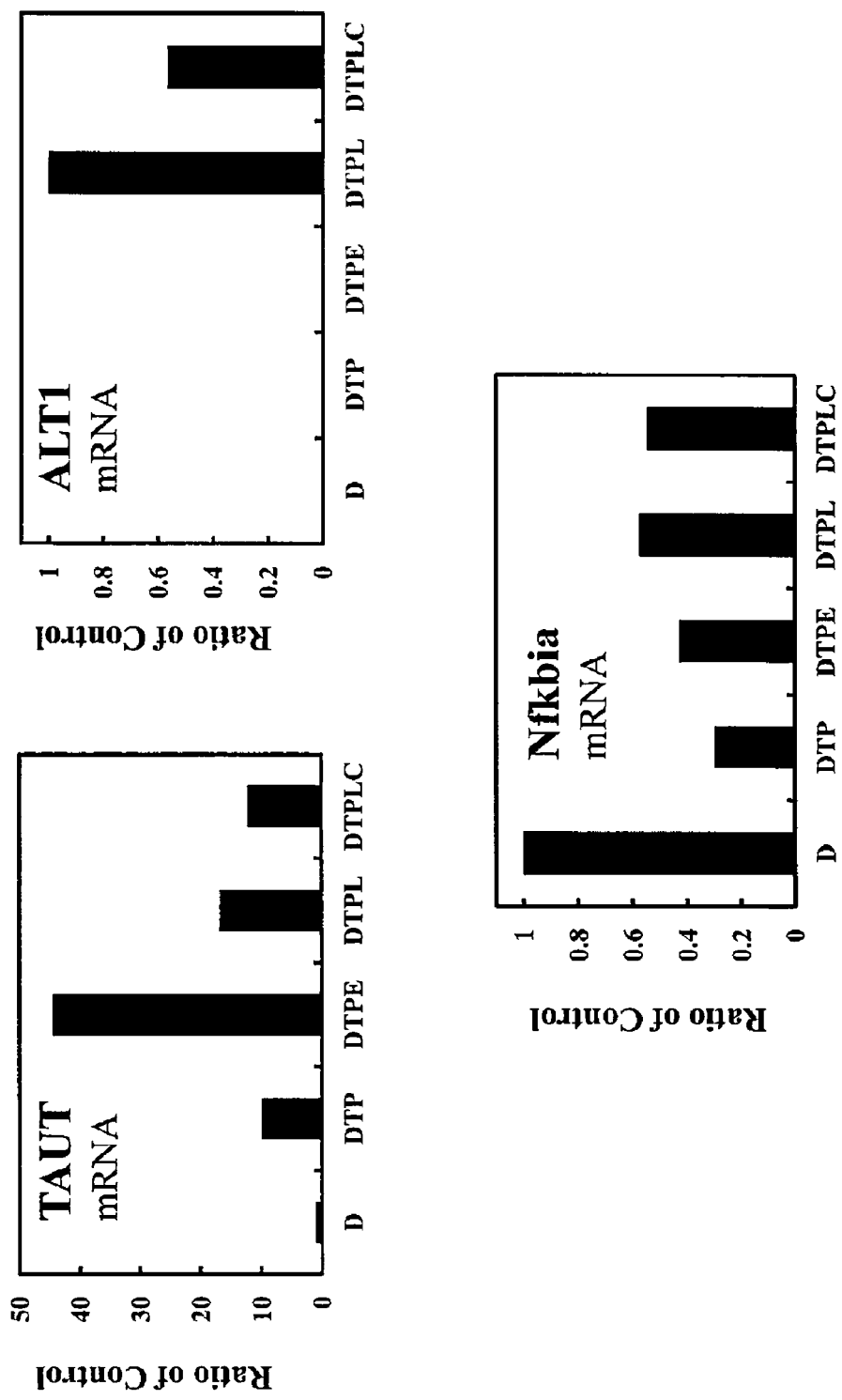
FIG. 27 shows the expression levels of hamster TAUT mRNA, human ALT1 mRNA, and Nfkbia mRNA (Example 1).

A hamster TAUT expression plasmid pHyg-TAUT was transferred to the host cells DXB11 by electroporation. Highly proliferative and highly hamster TAUT (taurine transporter)-expressing cells DXB11/TauT (DT) were established by screening in the presence of 200 µg/mL of hygromycin (FIG. 26). Further, an APES expression plasmid pPur-APES165 was transferred to the host cells by electroporation. Highly proliferative cells DXB11/TAUT/APES (DTP) in which Nfkbia mRNA expression was suppressed by the forced expression of APES (FIG. 26) were established by screening in the presence of 6 μg/mL of puromycin. The DTP cells were confirmed by the TAQMAN® method to stably maintain the high expression of hamster TAUT mRNA and the suppressed expression of Nfkbia mRNA even after repetitions of subculture (FIG. 27).

Example 1-2

Establishment of DXB11/TAUT/APES/AE1 Cell

Host cells highly co-expressing two transporters stably may be difficult to establish. For example, a stable line highly co-expressing TAUT and anion exchanger 1 (AE1) was not established from the host cells DXB11. A human AE1 expression plasmid pNeo-AE1 was transferred by electroporation to the highly hamster TAUT-expressing cells DXB11/TAUT/APES (DTP) in which Nfkbia mRNA expression was suppressed by the forced expression of APES as shown in FIG. 26. Highly proliferative cells DXB11/TAUT/APES/AE1 (DTPE) in which hamster TAUT and human AE1 were highly co-expressed were established by screening in the presence of 200 μg/mL of G418 (FIG. 28).

Figure 28:
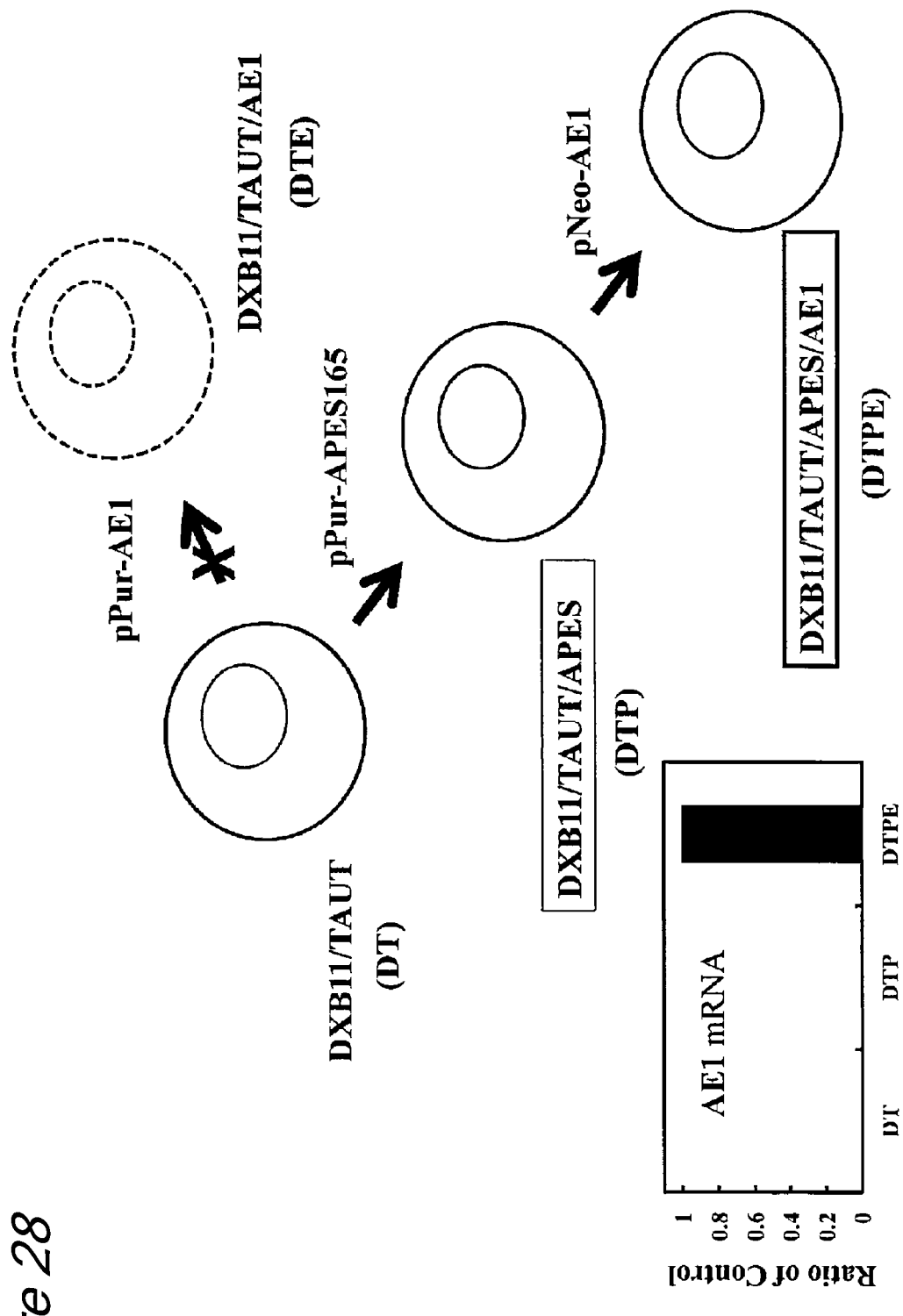
FIG. 28 shows the establishment of DXB11/TAUT/APES/AE1 (DTPE) host cells (Example 1).

The DTPE cells were confirmed by the TAQMAN® method to stably maintain the high expression of hamster TAUT mRNA, the high expression of human AE1 mRNA, and the suppressed expression of Nfkbia mRNA even after repetitions of subculture (FIGS. 27 and 28).

A human AE1 expression plasmid pPur-AE1 was transferred to the DXB11/TAUT (DT) cells by electroporation without transfer of APES. DXB11/TAUT/AE1 (DTE) cells were not established by screening in the presence of 6 μg/mL of puromycin.

Thus, the high co-expression of two transporters functioning cooperatively via the TAUT-mediated exit of Cl⁻ ions and the AE1-mediated uptake of Cl⁻ ions seems to require the suppression of Nfkbia mRNA expression by the high expression of APES.

Example 1-3

Establishment of DXB11/TAUT/APES/ALT1/PC Cell

Host cells highly co-expressing two enzymes stably may also be difficult to establish. For example, a stable line highly co-expressing alanine transferase (ALT1) and pyruvate carboxylase (PC) was not established from the host cells. A human ALT1 expression plasmid pNeo-ALT1 was transferred to DXB11/TauT/APES (DTP) of FIG. 26 by electroporation. Highly proliferative and highly human ALT1-expressing cells DXB11/TAUT/APES/ALT1 (DTPL) were established by screening in the presence of 200 μg/mL of G418. A human PC expression plasmid pZeo-PC was further transferred to the DTPL cells by electroporation. Highly proliferative and highly human PC-expressing cells DXB11/TAUT/APES/ALT1/PC (DTPLC) were established by screening in the presence of 200 μg/mL of Zeocin (FIG. 29).

Figure 29:
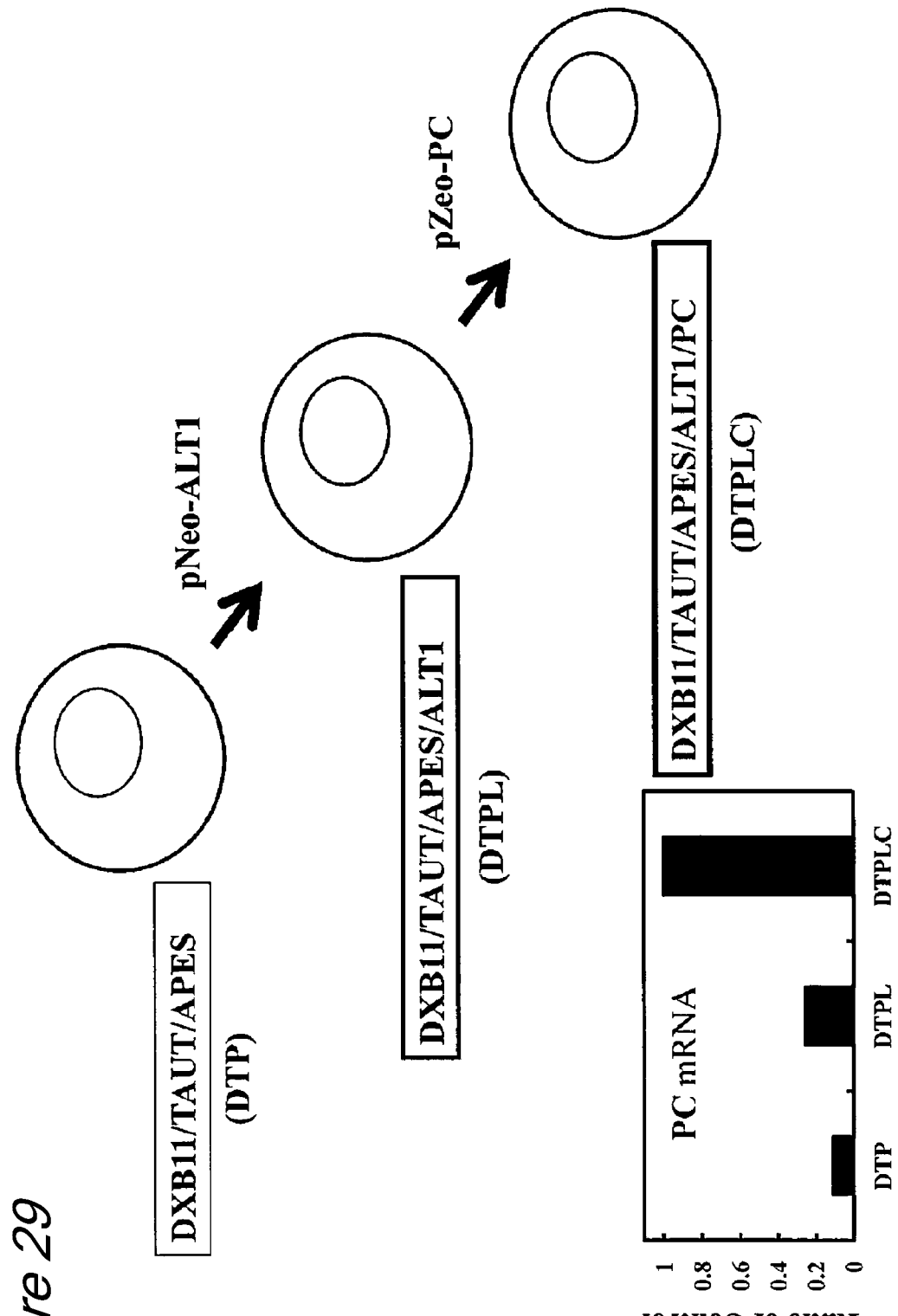
FIG. 29 shows the establishment of DXB11/TAUT/APES/ALT1/PC (DTPLC) host cells (Example 1).

The DTPLC cells were confirmed by the TAQMAN® method to stably maintain the high expression of hamster TAUT mRNA, the high expression of human ALT1 mRNA, the suppressed expression of Nfkbia mRNA, and the high expression of human PC mRNA even after repetitions of subculture (FIGS. 27 and 29).

Figure 30:
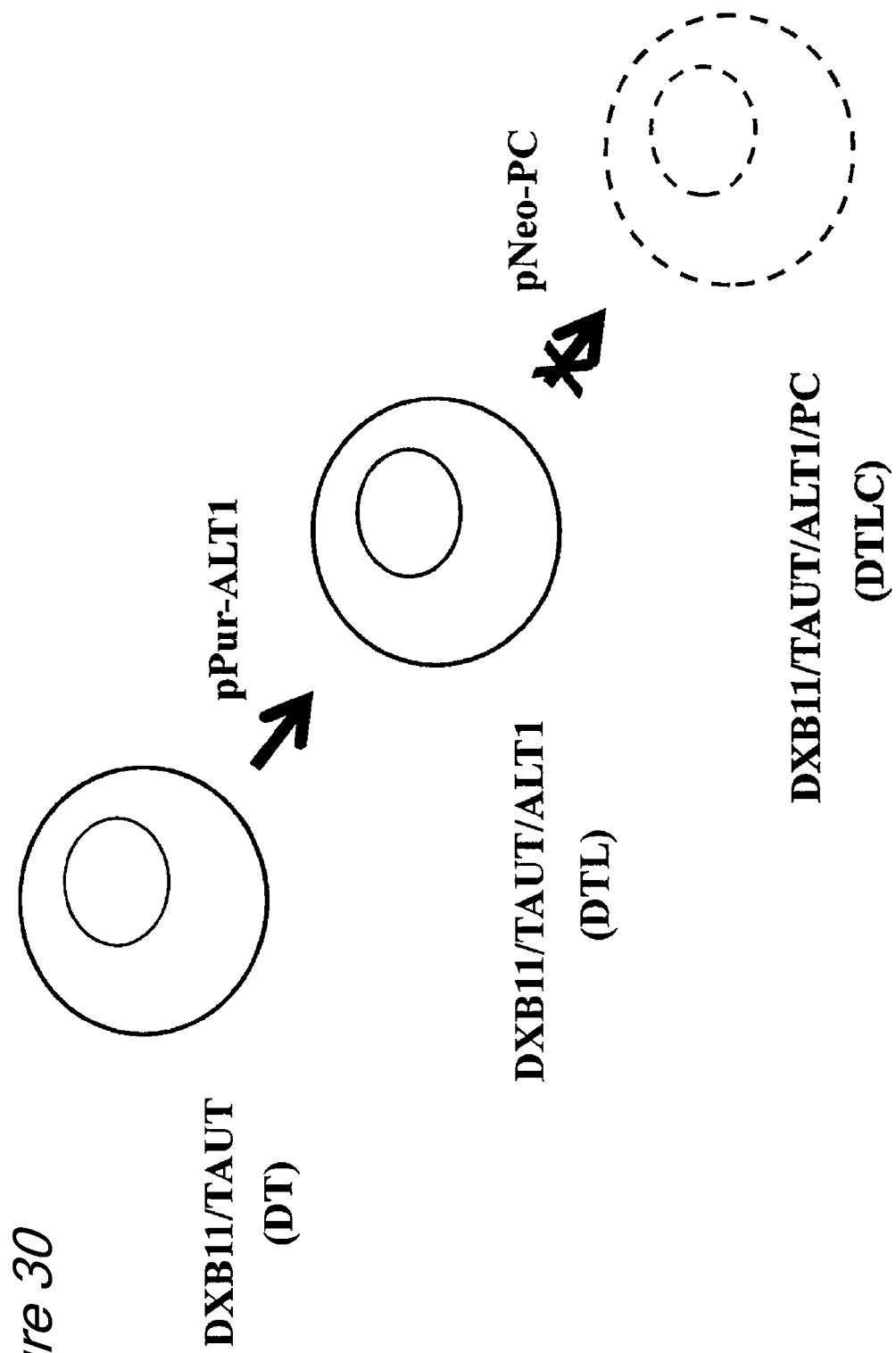
FIG. 30 shows that DXB11/TAUT/ALT1/PC (DTLC) host cells were not established even by the transfer of a human PC expression plasmid pNeo-PC to DXB11/TAUT/ALT1 (DTL) host cells (Example 1).

On the other hand, a human ALT1 expression plasmid pPur-ALT1 was transferred to the DXB11/TAUT (DT) cells by electroporation without transfer of APES. Highly proliferative and highly human ALT1-expressing cells DXB11/TAUT/ALT1 (DTL) were established by screening in the presence of 6 μg/mL of puromycin. A human PC expression plasmid pNeo-PC was further transferred to the DTL cells by electroporation. DXB11/TAUT/ALT1/PC (DTLC) was not established by screening in the presence of 200 μg/mL of G418 (FIG. 30).

Thus, the high co-expression of ALT1 and PC, enzymes promoting the continuous reactions of the pyruvate metabolism pathway, seems to require the suppression of Nfkbia mRNA expression by the high expression of APES.

Example 2

Method for Establishing Cell that Grows Stably with Short Doubling Time

Example 2-1

Calculation of Doubling Time (Estimate)

The doubling time (estimate) was calculated by shaker culture using a 125-mL Erlenmeyer flask followed by the measurement of the number of viable cells using Roche Cedex Cell Counter and Analyzer system (Innovatis AG, Bielefeld, Germany). From individual cells that maintained 90% or higher viability, subculture was started. Repetitive subculture operations were carried out by, for example, 3-day culture from an initial viable cell density of $2 \times 10^5$ cells/mL or 4-day culture from an initial viable cell density of $1 \times 10^5$ cells/mL so as to prevent overgrowth. The doubling time between passages was calculated while the viability was kept at 90% or higher. Although a subculture medium for modified cells having forced gene expression contained a drug such as hygromycin used in each gene transfer, the same medium as that for DXB11 (dhfr-) was used except for the drug.

Figure 31:
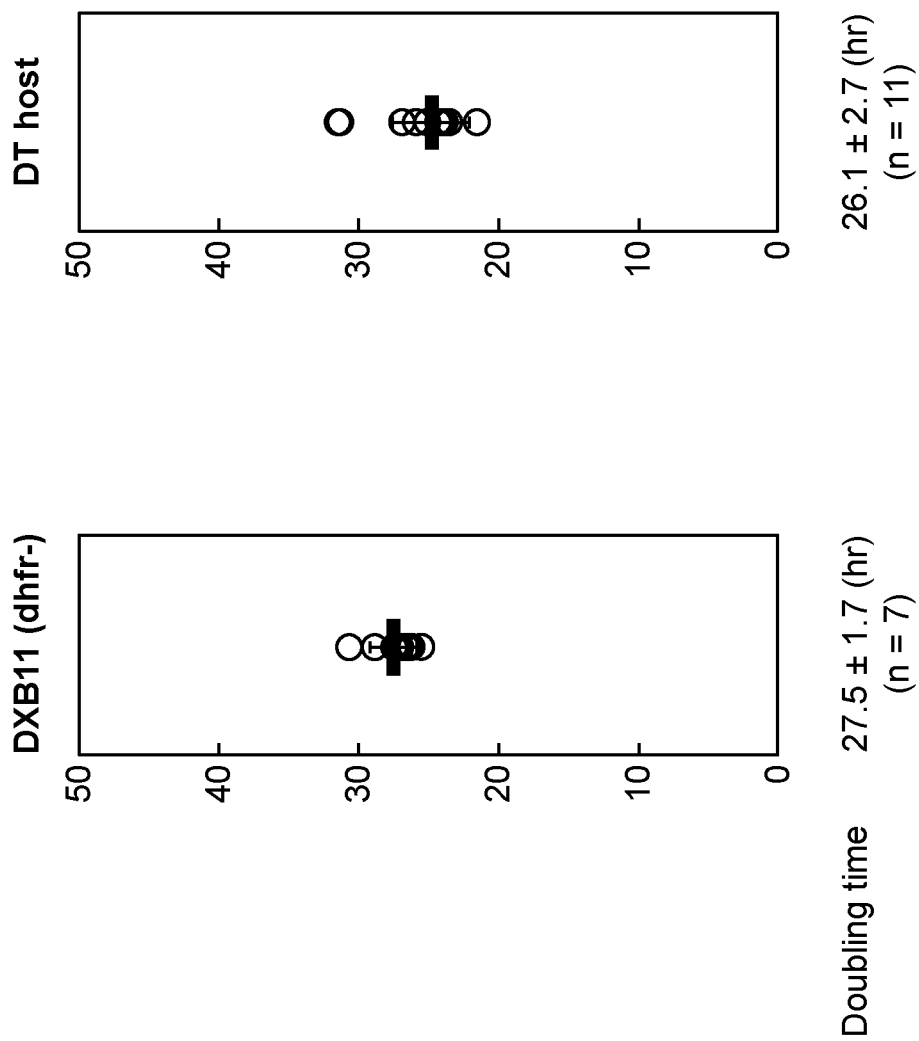
FIG. 31 shows the doubling times of DXB11 (dhfr-) and a DT host cell (Example 2).

The doubling time (estimate) of DXB11 (dhfr-) before modification based on gene transfer was calculated for subculture in a drug-free medium (7 subculture operations (four 3-day culture runs and three 4-day culture runs) from cells having 99.5% viability) and consequently determined to be 27.5±1.7 hours (FIG. 31).

Example 2-2

Establishment of Hosts Forced to Express Various Genes and Doubling Time

Figure 32:
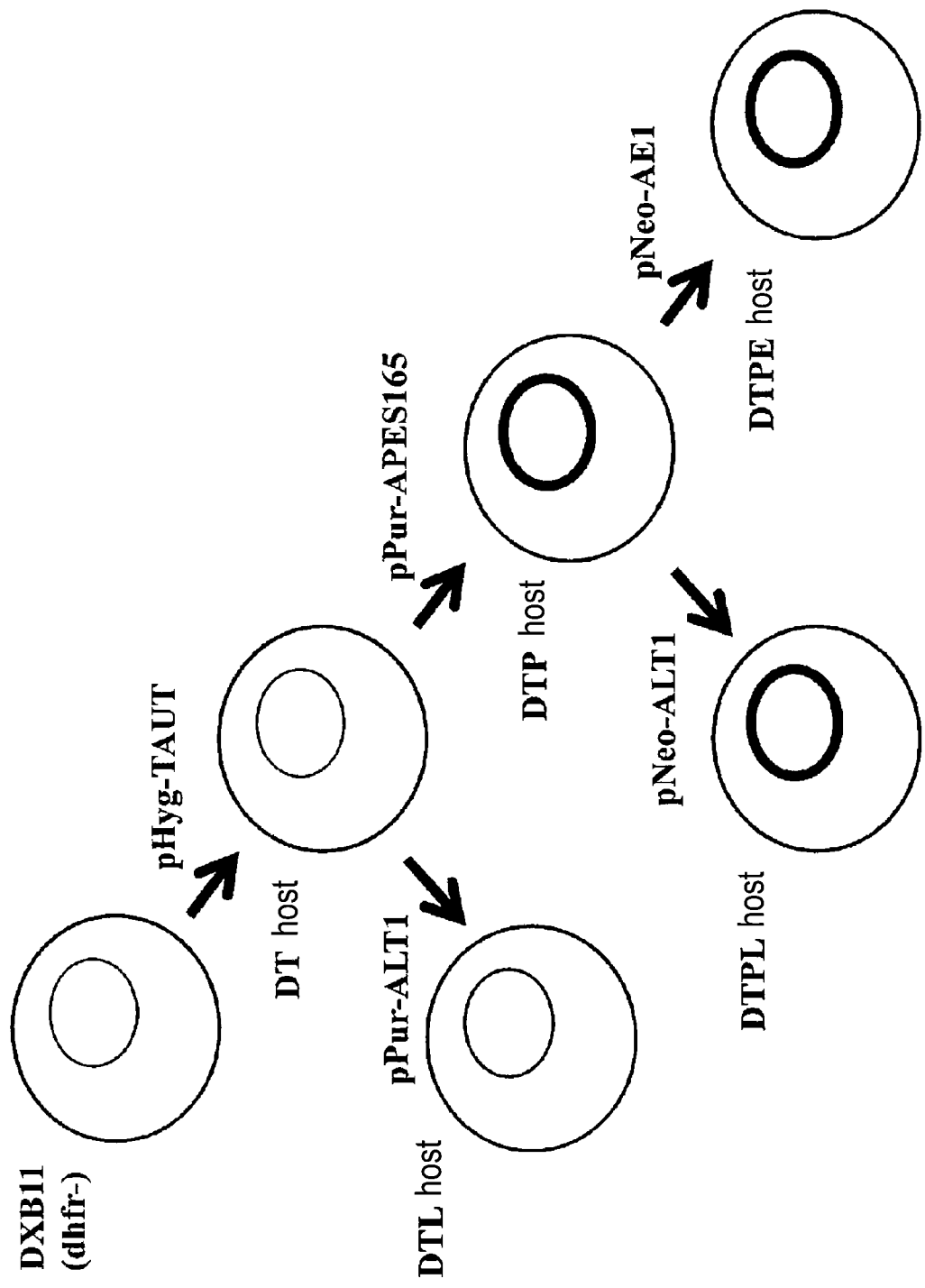
FIG. 32 shows the preparation of modified host cells by the forced overexpression of various genes (Example 2).

As shown in FIG. 32, modified hosts were established by the forced expression of various genes. First, the taurine transporter (TAUT) expression plasmid (pHyg-TAUT) was transferred to DXB11 (dhfr-) by electroporation. Approximately 2 to 3 weeks later, two lines of favorably grown cells were selected in the presence of 200 μg/mL of hygromycin. Their gene expression profiles at the time of subculture were compared with those of the unmodified line by a GENECHIP® experiment using an oligonucleotide array from Affymetrix, Inc. (Affymetrix MOUSE430_2) to select, as a DT host, a line highly expressing TAUT mRNA and having other expression profiles similar to those of DXB11 (dhfr-). The doubling time (estimate) of the established DT host was calculated for subculture in a drug (hygromycin)-containing medium (11 subculture operations (four 3-day culture runs and seven 4-day culture runs) from cells having 90.0% or higher viability) and consequently determined to be 26.1±2.7 hours, which was substantially equivalent to the doubling time of DXB11 (dhfr-) (FIG. 31).

Figure 20:
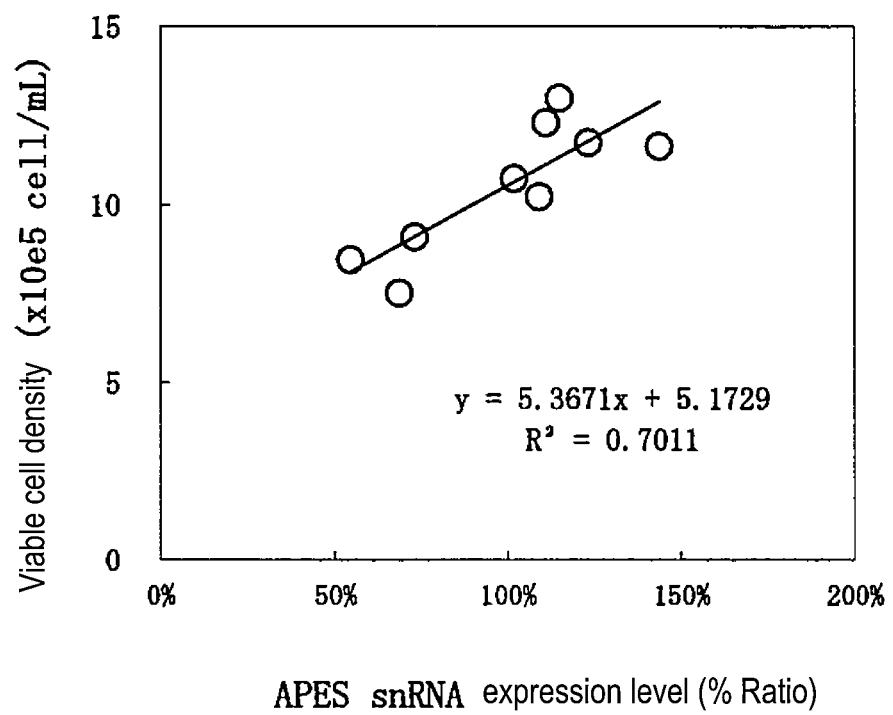
FIG. 20 shows the correlation between the APES expression levels of APES165-overexpressing candidate host cells (9 lines) and their viable cell densities (Reference Example 6).

Next, for the further modification of the DT host, a partial sequence APES165 (Japanese Patent Application No. 2011-082002) of APES, which is abnormally overexpressed in mAb-producing cells, was forcedly expressed. The pPur-APES165 was transferred to the DT host by electroporation. Approximately 2 to 3 weeks later, 9 lines of favorably grown cells were selected in the presence of 6 μg/mL of puromycin. The correlation between the APES expression level and cell growth (R2=0.701) was observed (FIG. 20).

Figure 33:
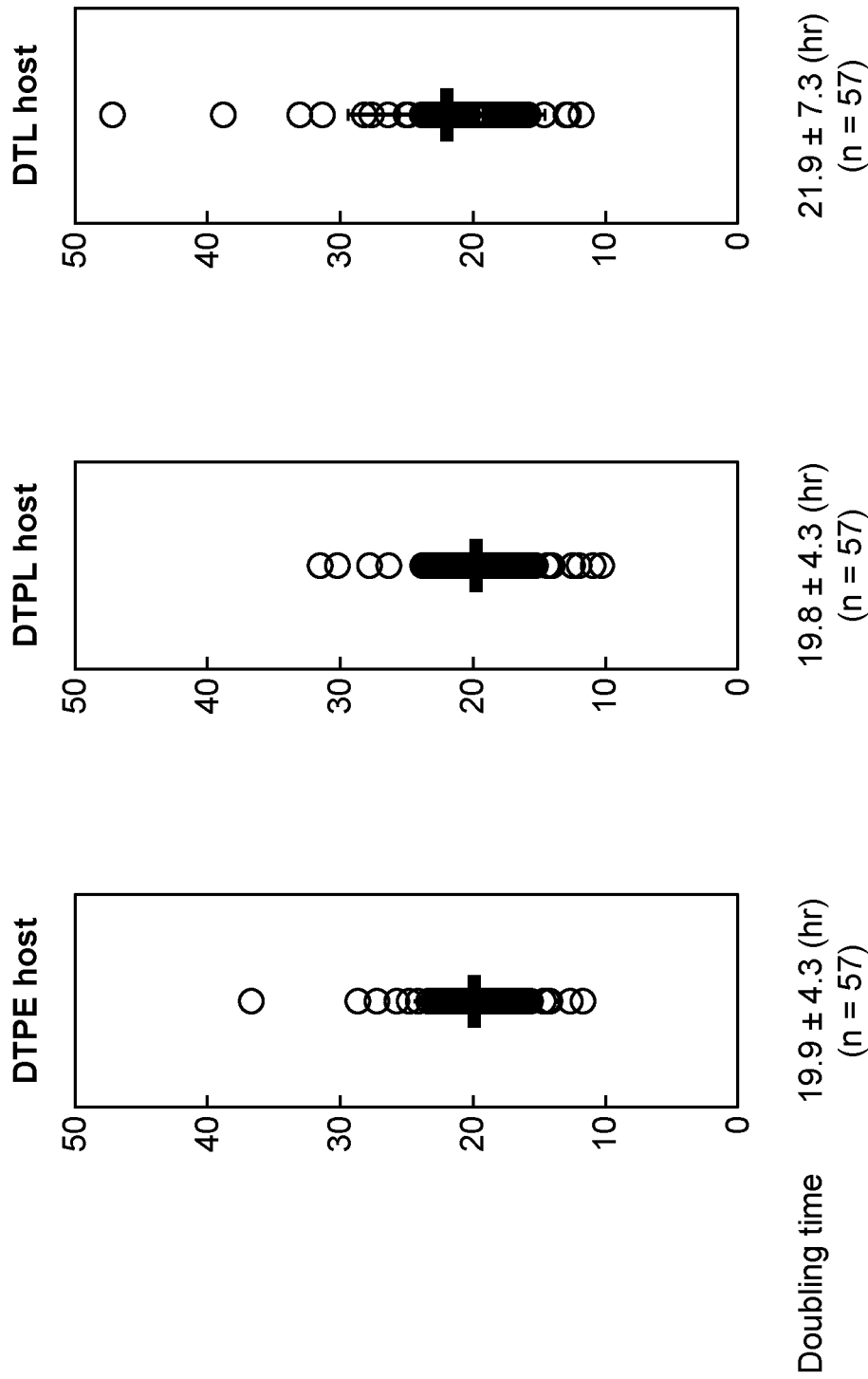
FIG. 33 shows the doubling times of modified host cells (Example 2).

When a cell line highly co-expressing TAUT and APES and having the shortest doubling time of 20.8 hours was used as a DTP host, this DTP host acquired unprecedented characters. For example, the anion exchanger 1 (AE1) expression plasmid (pNeo-AE1), which failed to establish host cells forced to co-express AE1 and TAUT, was transferred to the DTP host by electroporation. Approximately 2 to 3 weeks later, favorably grown cells were selected in the presence of 200 μg/mL of G418 to construct cells highly co-expressing TAUT and AE1. When a cell line having the highest AE1 expression level was used as a DTPE host, this DTPE host was stable even after repetitions of culture for a long period and had a doubling time shorter than that of the DTP host (FIG. 33, 57 passages, 19.9±4.3 hours).

As a subsequent example, the alanine aminotransferase 1 (ALT1) expression plasmid (pNeo-ALT1), which was able to establish host cells forced to co-express ALT1 and TAUT, was transferred to the DTP host by electroporation. Approximately 2 to 3 weeks later, favorably grown cells were selected in the presence of 200 μg/mL of G418 to construct cells highly co-expressing TAUT and AE1. Since the correlation between the ALT1 expression level and cell growth was found, a cell line having the highest ALT1 expression level was used as a DTPL host. This host was also stable even after repetitions of culture for a long period and had a doubling time shorter than that of the DTP host (FIG. 33, 57 passages, 19.8±4.3 hours). Since host cells forced to co-express ALT1 and TAUT can be established independently of the forced expression of APES, the ALT1 expression plasmid (pPur-ALT1) was transferred to the DT host by electroporation. Approximately 2 to 3 weeks later, favorably grown cells were selected in the presence of 6 μg/mL of puromycin. When a cell line having the highest ALT1 expression level was used as a DTL host, this DTL host was stable even after repetitions of culture for a long period, but was confirmed to grow nonuniformly compared with the DTPL host and to have a doubling time longer than that of the DTPL host (FIG. 33, 57 passages, 21.9±7.3 hours).

These results indicate that: (1) host cells with a short doubling time can be constructed by the forced overexpression of APES; and (2) cells with a shorter doubling time can be constructed by the further transfer of another gene to the strongly APES-expressing host. The nucleic acid sequence having such functions was previously unknown.

REFERENCE EXAMPLES

The present inventors previously used a cultured cell line (CHO cell line) having the high ability to produce recombinant antibodies as a material to study a gene that exhibited marked expression in this cell line, thereby identifying one mRNA-type non-coding RNA. This transcript corresponded to a complementary strand of the untranslated region of NfkBia mRNA. The present inventors further found that the ability of cultured recombinant cells to produce antibodies can be remarkably improved by the expression of a nucleic acid molecule consisting of a partial sequence in this transcript in the cultured cells. The present inventors also found that: the expression of NfkBia is suppressed in highly mAb-producing cells having a rise in the expression of the non-coding RNA; the expression of NfkBia is suppressed in cultured cells having the high ability to produce mAbs; and the yield of mAbs is increased by the high expression of the transcript controlling the expression of NfkBia in the cultured cells.

These matters will be described with reference to the following Reference Examples.

Reference Example 1

GENECHIP® Experiment to Analyze Various Transgenic CHO Cells

The GENECHIP® experiment was conducted according to routine procedures using an oligonucleotide array from Affymetrix, Inc. (Affymetrix MOUSE430_2). However, since any hamster array was commercially unavailable, Mouse Genome 430 2.0 Array was used instead. The optimization of hybridization conditions resulted in detectable present calls in 8 of 16 mouse gene probes on Test 3 array and thus enabled the expression of transcripts in hamsters to be quantified when their nucleotide sequence homology to mouse sequences was approximately 90% or higher.

High-purity total RNA was prepared from cells strongly expressing various genes. Then, cDNA was synthesized using the total RNA and an oligo dT primer containing a T7 promoter sequence (T7-(T)24). Next, biotin-labeled cRNA was synthesized from the cDNA through transcription reaction using Bio-11 CTP, Bio-16 UTP, and MEGASCRIPT® T7 Kit (Ambion). After column purification of the cRNA, high-quality cRNA confirmed to have a molecular weight corresponding to 18s to 28s rRNA on electrophoresis was fragmented to prepare GENECHIP® samples having a uniform size. The GENECHIP® samples were supplemented with a hybridization sample solution and cryopreserved at −80° C. until use. Each sample solution was heat-treated immediately before use, centrifuged, and applied to Mouse Genome 430 2.0 Array. The sample was incubated at 45° C. for 16 hours in an oven specialized for hybridization, with the array rotated. The sample was recovered, and the array was repeatedly washed, stained with streptavidin R-phycoerythrin, and then scanned.

The GENECHIP® signal values of the transcripts (approximately 45,000) on the arrays were compared. As a result, an mRNA-type non-coding RNA UG_GENE=AI462015 (Affymetrix MOUSE430_2, 1420088_AT) on the mouse genome was identified as a transcript overexpressed with high intensity in strongly MAb1 (anti-IL-6R antibody)-expressing, TAUT-overexpressing, and CSAD-overexpressing subcultured DG44 cells that produced 900 mg/L or more of MAb1 (anti-IL-6R antibody; tocilizumab, trade name: ACTEMRA®) on day 10 of the 1 L-jar feeding culture (FIG. 1: the sequence of the AI462015 transcript).

AI462015 is a 437-base mRNA-type non-coding RNA whose sequence resides on the complementary strand near the 3′-untranslated region (56590831-56590397) of NfkBia mRNA in chromosome 12 on the mouse genome. The possibility was suggested that the AI462015 transcript would act directly on the untranslated region of NfkBia mRNA to inhibit the translation or that a portion of the 437-base sequence would function as a small RNA to degrade NfkBia mRNA.

For example, a 52-base sequence comprising A at nucleotide 40 through A at nucleotide 91 from the 5' end (AAGTACCAAAATAATTACCAACAAAATACAA-CATATACAACATTTACAAGAA: SEQ ID NO: 7) in the AI462015 sequence matches with the complementary strand of the 3'-untranslated region (1478-1529, GENE ID: 25493 NfkBia) of rat NfkBia mRNA except for one base (A at nucleotide 61 from the 5' end in AI462015). In addition, a 24-base sequence comprising A at nucleotide 40 through A at nucleotide 63 (AAGTACCAAAATAATTACCAACAA: SEQ ID NO: 9) in AI462015 is the complementary strand of a partial sequence (TTGTTGGTAATTATTTTGGTACTT, 1490-1513: SEQ ID NO: 24) of the 3'-untranslated region of human NfkBia mRNA. It was therefore predicted that 19 to 25 bases, a portion of the 52-base sequence, as a microRNA or a partial sequence thereof as an antisense RNA could act on the NfkBia mRNA of CHO cells.

The updated information of GenBank further revealed that the 437-base transcript of AI462015 corresponds to the complementary strand of the 3'-untranslated region (513 bases) of the mouse NfkBia gene (FIG. 23). As shown in FIG. 24, the homologous sequence of AI462015 resides on the genomic sequence of CHO-K1 cells (SEQ ID NO: 25: AI462015; SEQ ID NOs: 26-27: CHO-K1 genome). In addition, suppressed Nfkbia expression (Reference Example 4) was observed in highly antibody-producing CHO cells, suggesting that the homologous sequence of AI462015 is highly expressed functionally in CHO cells.

Figure 25E:
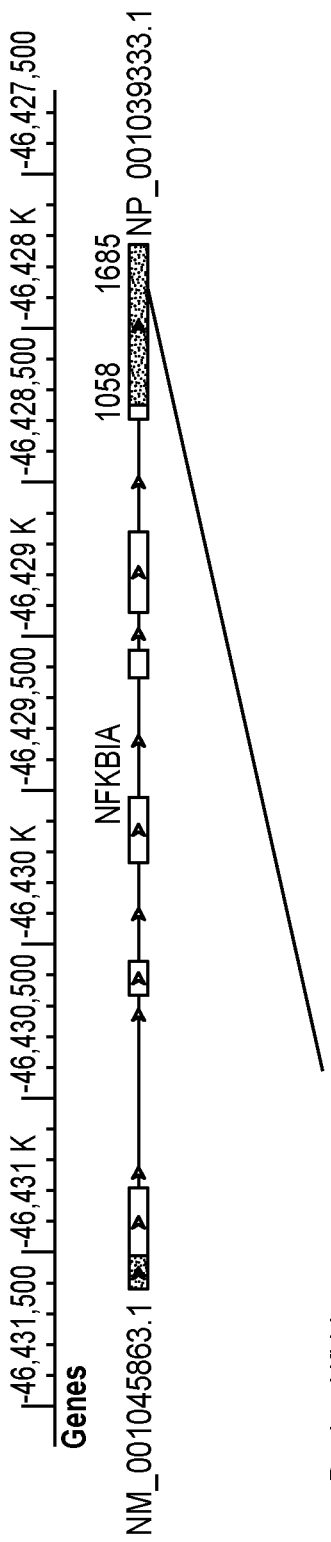
FIG. 25*e* shows that a partial sequence (nucleotides 7 to 91 from the 5' end) of AI462015 is conserved regardless of species (Reference Example 1).

For example, an 85-base sequence comprising T at nucleotide 7 through A at nucleotide 91 from the 5' end (underlined in FIGS. 23 and 24, SEQ ID NO: 29) (TGTAAAAATCTGTTTAATAAATATACATCT-TAGAAGTACCAAAATAATTACCAACAAAATA CAA-CATATACAACATTTACAAGAA) in the AI462015 sequence matches with the complementary strand of the 3'-untranslated region (1478-1562, GENE ID: 25493 NfkBia, SEQ ID NO: 31) of rat NfkBia mRNA except for one base (A at nucleotide 70 from the 5' end in AI462015) (Matching=84/85, FIG. 25b). Likewise, this sequence was confirmed to be homologous to human (Matching=75/85, FIG. 25a, SEQ ID NO: 30), chimpanzee (Matching=75/85, FIG. 25c, SEQ ID NO: 32), rhesus monkey (Matching=74/85, FIG. 25d, SEQ ID NO: 33), and bovine (Matching=76/85, FIG. 25e, SEQ ID NO: 34) sequences. Accordingly, 19 to 25 bases, a portion of the 85-base sequence (Conserved Sequence 7-91), as a microRNA or a partial sequence thereof as an antisense RNA is considered to act on animal cells or mammalian cells regardless of species. Thus, it was predicted that this microRNA or antisense RNA would also act on the NfkBia mRNA of cultured animal cells, preferably mammalian cells such as CHO cells.

Reference Example 2

Identification of Transcript Overexpressed in Highly mAb-Producing Cell

Figure 2:
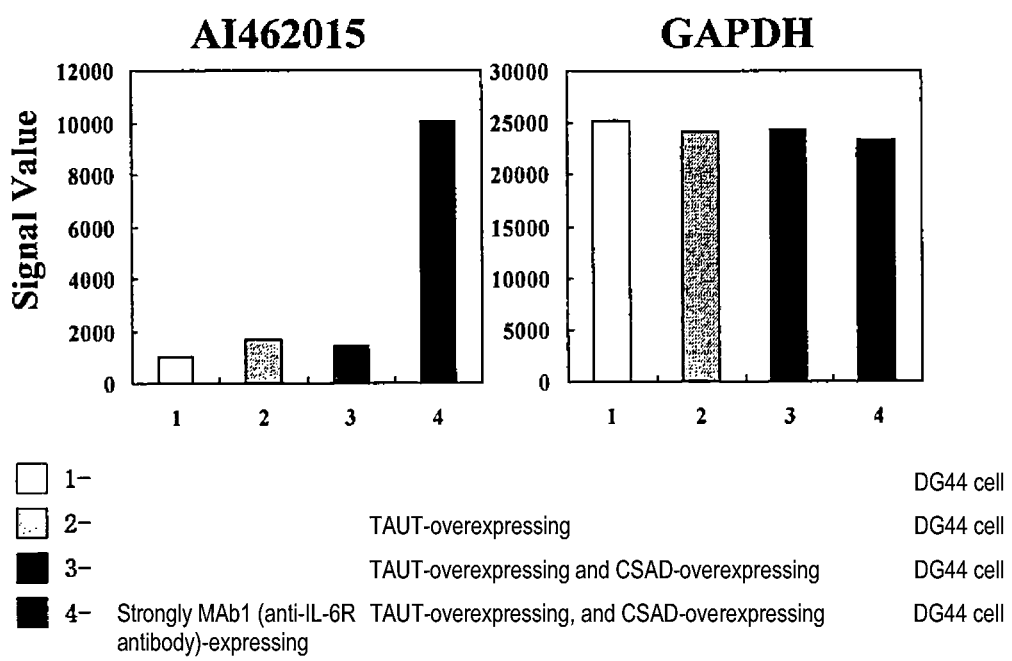
FIG. 2 shows the expression intensity of the AI462015 transcript on day 3 of the subculture of antibody-producing cells in which MAb1 (anti-IL-6 receptor antibody) was highly expressed by CHO-DG44 cells (Reference Example 2).
Figure 3:
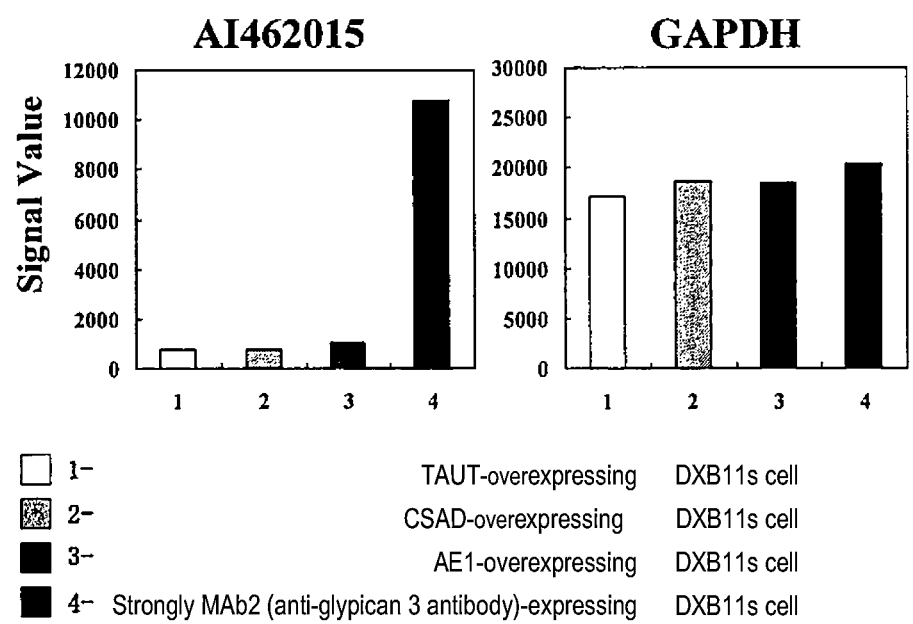
FIG. 3 shows the expression intensity of the AI462015 transcript on day 3 of the subculture of antibody-producing cells in which MAb2 (anti-glypican 3 antibody) was highly expressed by CHO-DXB11s cells (Reference Example 2).

In Reference Example 1, the expression level of the transcript AI462015 was increased in the DG44 cells highly producing MAb1 (anti-IL-6R antibody: tocilizumab, trade name: ACTEMRA®) (FIG. 2). Likewise, the overexpression of the AI462015 transcript was also observed when a different mAb (MAb2: anti-glypican 3 antibody; GC33 (see WO2006/006693)) was highly produced in different host cells (CHO-DXB11s) (FIG. 3).

As shown in FIG. 2, the expression level of the transcript AI462015 was equivalent among CHO-DG44 cells overexpressing the taurine transporter (TAUT) gene, CHO-DG44 cells overexpressing the cysteine sulfinic acid decarboxylase (CSAD) gene (data not shown), and CHO-DG44 cells co-overexpressing TAUT and CSAD. By contrast, abnormally overexpressed AI462015 (7 times its expression in the host cells) was observed in cells co-overexpressing TAUT and CSAD and further strongly expressing Mab1 (anti-IL-6 receptor antibody), and its expression level also exhibited an abnormally high GENECHIP® signal value (10,000 or higher). Since these cells had the same level of GAPDH expression intensity as a control, the overexpression of the transcript AI462015 was specific for the cells highly producing the Mab1 antibody. The same holds true for FIG. 3. When the MAb2 (anti-glypican 3 antibody) gene was strongly expressed in CHO-DXB11s cells, the overexpression of the AI462015 sequence (13 times the average value of cells overexpressing TAUT, CSAD, or AE1) was specific for the cells highly producing the MAb2 antibody.

These results indicate that highly antibody-producing cells that grow stably on day 3 of the shaker passage culture express the AI462015 sequence at an abnormally high level.

Figure 4:
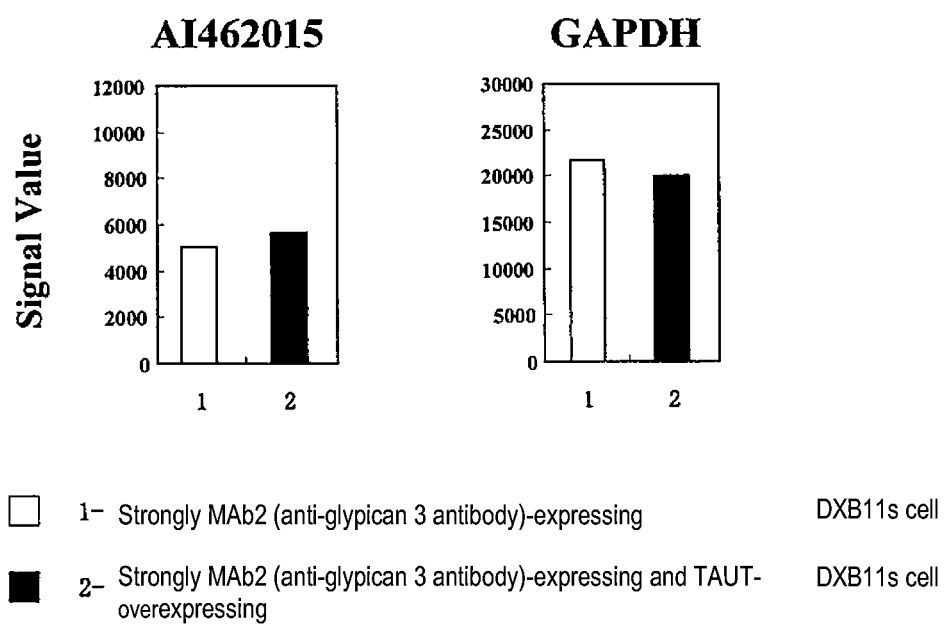
FIG. 4 shows the expression intensity of the AI462015 transcript on day 3 of the 1 L-jar fed-batch culture of MAb2 (anti-glypican 3 antibody)-producing cells (Reference Example 2).
Figure 5:
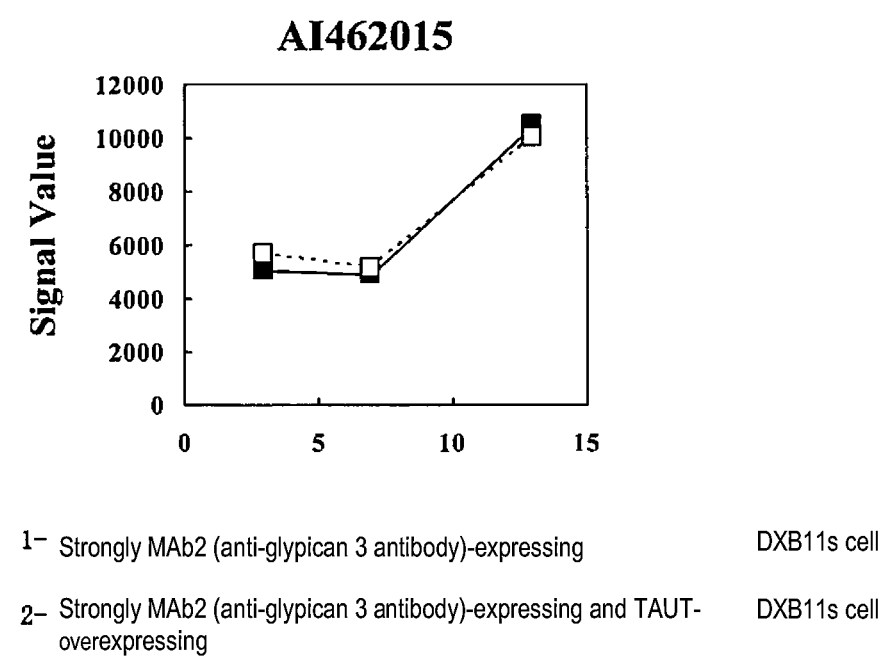
FIG. 5 shows a rise in the expression intensity of the AI462015 transcript on day 13 at the late stage of the 1 L-jar fed-batch culture of MAb2-producing cells (Reference Example 2).

Under production culture conditions on day 3 of the 1 L-jar culture, the abnormal overexpression of the AI462015 sequence was also observed. As shown in FIG. 4, two lines of highly antibody-producing cells that produced approximately 1200 to 1400 mg/L of MAb1 (anti-IL-6R antibody) on day 10 of the 1 L-jar fed-batch culture exhibited a high GENECHIP® signal value of 5,000 or higher. Although the GENECHIP® signal value on day 3 of the 1 L-jar fed-batch culture was approximately 50% of the value in the shaker culture due to the difference in culture conditions, the expression intensity of the AI462015 sequence was increased to a level comparable to that in the shaker passage culture on day 13 at the late stage of the 1 L-jar fed-batch culture, showing an abnormally high signal value (FIG. 5). On the other hand, strongly MAb1-expressing DXB11s cells with a low antibody yield (300 mg/L or less on day 7 of hydrolysate-free shaker culture; 500 mg/L or less even in hydrolysate-supplemented culture) were not confirmed to overexpress the AI462015 sequence on day 3 of the 1 L-jar culture even under conditions where a hydrolysate contributing to higher production (Hy-Fish or porcine lysate) was added (FIG. 6).

Figure 6:
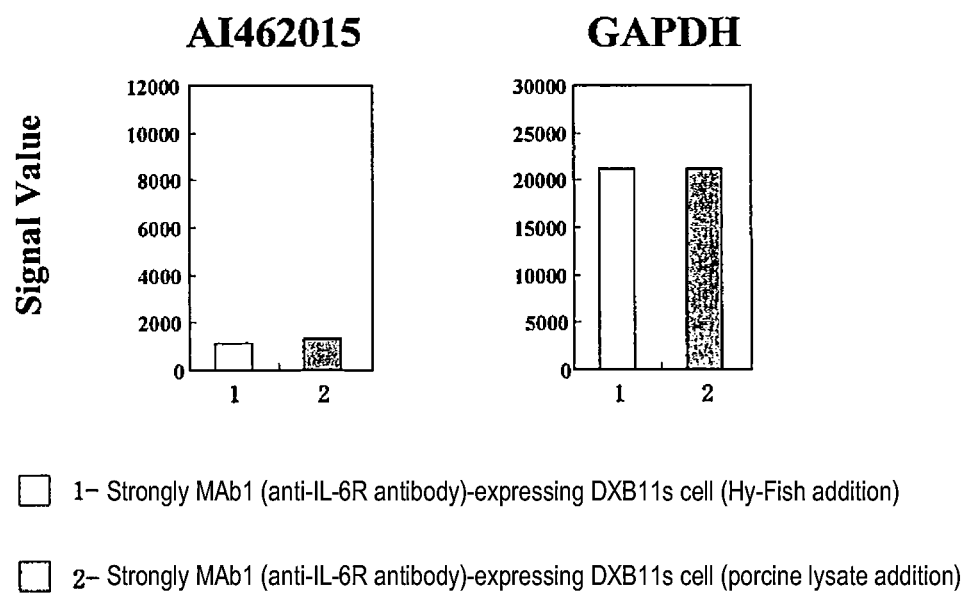
FIG. 6 shows the expression intensity of the AI462015 transcript on day 3 of the 1 L-jar fed-batch culture of cells having the low potential to produce MAb1 (anti-IL-6 receptor antibody) (Reference Example 2).

These experimental results showing the high antibody yield (640 mg/L on day 7 of the hydrolysate-free shaker culture) in the strongly MAb1-expressing, TauT-overexpressing, and CSAD-overexpressing DG44 cells that exhibited a high signal value in FIG. 2, the high antibody yield (640 mg/L on day 7 of the hydrolysate-free shaker culture) in the strongly MAb2-expressing DXB11s cells that exhibited a high signal value in FIG. 3, and no rise in signal value even under conditions where a hydrolysate contributing to higher antibody production was added in FIG. 6, suggested that "cells having a high expression level of the AI462015 sequence have the high potential to produce antibodies".

Reference Example 3

Example of Higher Production Resulting from APES Overexpression in mAb-Producing Cell In order to demonstrate that the high expression level of the AI462015 sequence correlates with the high potential to produce antibodies, each plasmid for the expression of a portion of the AI462015 sequence was transferred to the strongly MAb1-expressing DXB11s cells having the low potential to produce mAbs in FIG. 6. After strong expression, the potential to produce mAbs was compared among the cell lines.

Figure 7:
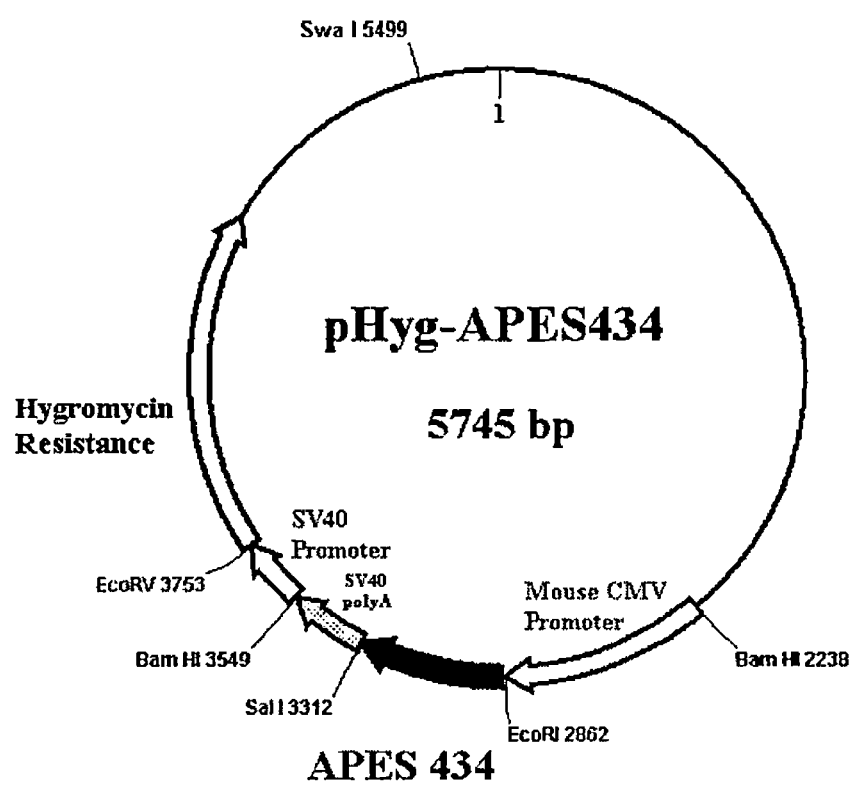
FIG. 7 shows an expression plasmid of a partial sequence 434 bp of the transcript AI462015 (437b) (Reference Example 3).
Figure 8:
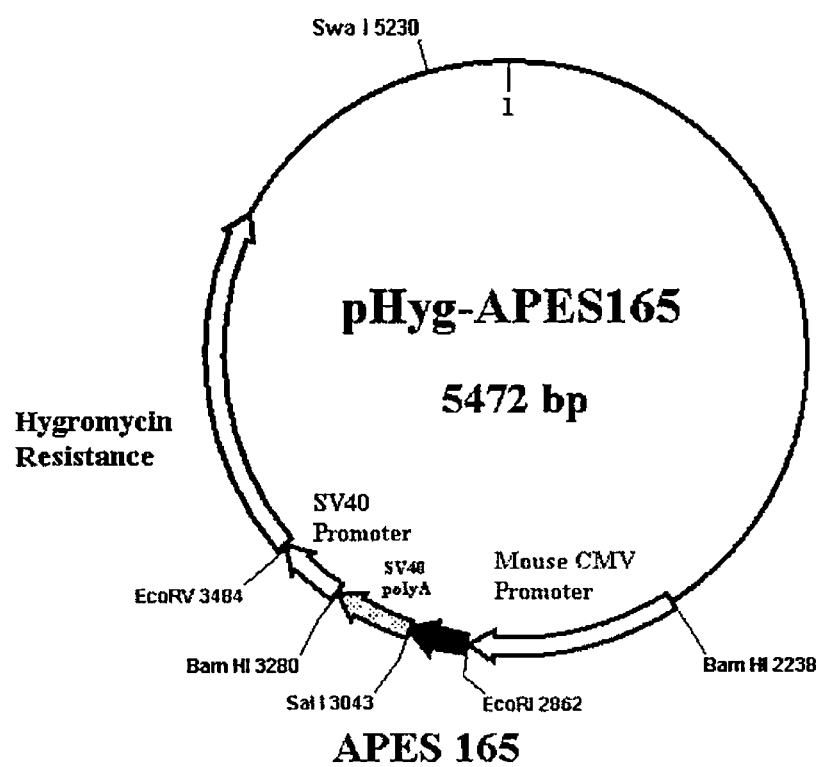
FIG. 8 shows an expression plasmid of a partial sequence 165 bp of the transcript AI462015 (437b) (Reference Example 3).
Figure 9:
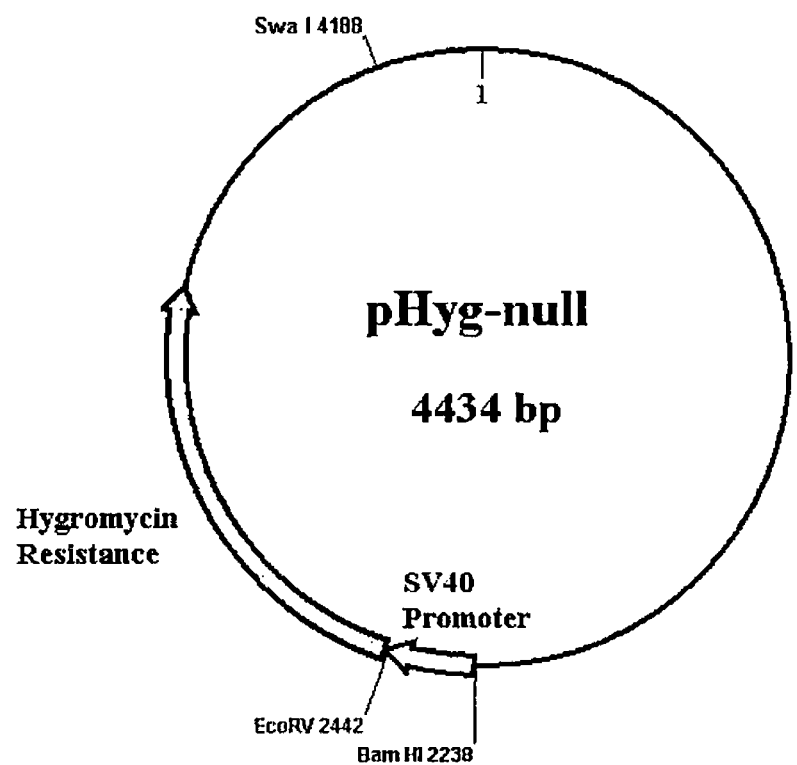
FIG. 9 shows a control plasmid used for the expression of only a hygromycin resistance gene (Reference Example 3).

In the sequence of the mouse genome-derived transcript AI462015 (FIG. 1, 437 bases), partial sequences (containing the AI462015 probe sequence of Affymetrix GENECHIP®) from G at nucleotide 4 from the 5' end to T at the 3' end and from G at nucleotide 4 and C at nucleotide 168 from the 5' end were designated as APES434 and APES165, respectively, and two types of expression units were prepared therefrom (APES: an abbreviation for antibody production enhancing sequence). These expression units further having Kozak sequence were synthesized to construct pHyg-APES434 (FIG. 7) and pHyg-APES165 (FIG. 8), each of which was to be highly expressed under the control of CMV promoter, and pHyg-null (FIG. 9).

Figure 10:
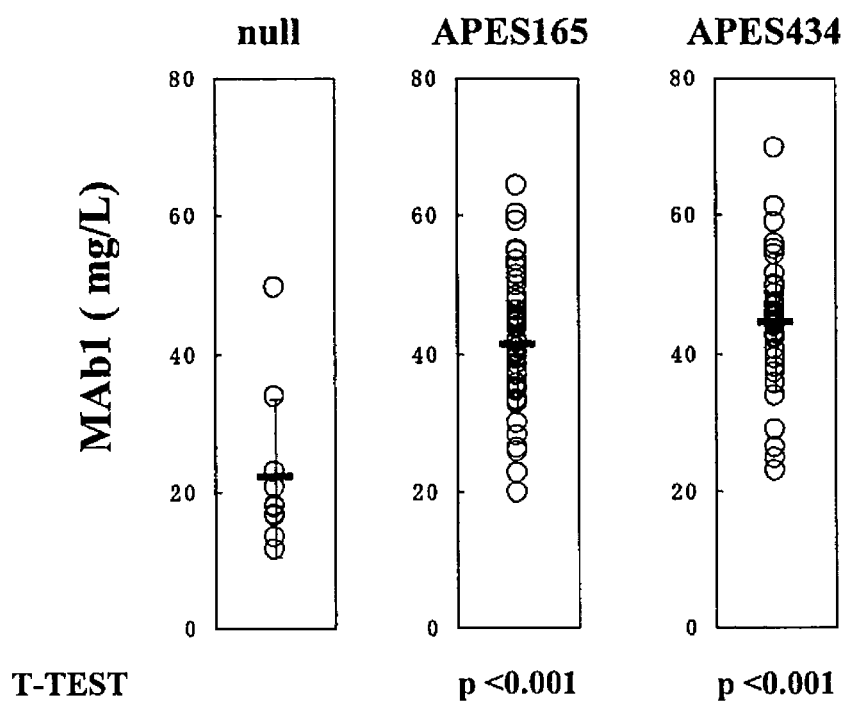
FIG. 10 shows that the Mab1 yield is increased by the strong expression of a partial sequence of the transcript AI462015 (437b) (Reference Example 3).

A gene transfer system NUCLEOFECTOR® from Amaxa (currently, Lonza Group Ltd.) was used to transfer the expression plasmids to the strongly MAb1-expressing DXB11s cell lines with a low antibody yield in FIG. 6. All cell lines that highly grew on 96-well plates in the presence of a selection medium containing hygromycin (200 µg/ml) were selected and expanded to 24-well plates. Then, the mAb yield was compared among these cell lines. The numbers of the selected lines were pHyg-APES434 (N=38), pHyg-APES165 (N=60), and pHyg-null (N=11) and were expected to produce a positive effect from the transfer of the plasmids for strong APES expression. Since no cell growth was observed on day 13 of the static culture in the 24-well plates containing 1 mL of a subculture medium, the antibody yield and the cell count were measured. The average antibody yield was pHyg-APES434 (44.3 mg/L), pHyg-APES165 (41.2 mg/L), and pHyg-null (21.9 mg/L), and the average cell count was pHyg-APES434 ($9.27 \times 10^5$ cells/mL), pHyg-APES165 ($11.39 \times 10^5$ cells/mL), and pHyg-null ($7.76 \times 10^5$ cells/mL). The pHyg-APES434-transferred cells and the pHyg-APES165-transferred cells were both statistically superior to the control pHyg-null-transferred cells (t-test, P<0.001, FIG. 10).

These results demonstrated that the potential of cells to produce antibodies was enhanced by the overexpression of the nucleic acid sequence comprising the 5' 165 bp of the AI462015 transcript (e.g., APES165, which is the DNA transcript of SEQ ID NO: 2, or APES434, which is the DNA transcript of SEQ ID NO: 3).

Reference Example 4

Suppression of NfkBia Expression in Highly Antibody-Producing CHO Cell

As mentioned in Reference Example 1, the AI462015 sequence resides on the complementary strand near the 3'-untranslated region (3' 78 bp) of the NfkBia gene in chromosome 12 on the mouse genome; and the 22-base sequence (AAGTACCAAAATAATTACCAAC: SEQ ID NO: 10) contained in the AI462015 sequence is identical to the complementary strand of the 3'-untranslated region (1492-1513) of the human NfkBia gene and is further conserved regardless of species such as rats, rhesus monkeys, dogs, and horses, suggesting that this 22-base sequence can work as a microRNA to degrade NfkBia mRNA through RNA interference. In addition, the 21-base sequence (CATATACAACATTTACAAGAA: SEQ ID NO: 15) from C at nucleotide 71 from the 5' end, which corresponds to the former part of the specific probe sequence region (42-base) (CATATACAACATTTA-CAAGAAGGCGACACAGACCTTAGTTGG: SEQ ID NO: 16) on an oligonucleotide array from Affymetrix, Inc. (Affymetrix MOUSE430_2) capable of quantifying AI462015 expression, is complementary to the sequence from nucleotides 1478 to 1498 of rat NfkBia mRNA, suggesting that the AI462015 sequence-derived nucleic acid molecule can suppress NfkBia expression through the RNA interference of NfkBia mRNA and thereby maintain the homeostasis of highly antibody-producing CHO cells (lethality of knockout mice: postnatal) (Note: the AI462015 transcript was found later to correspond to the complementary strand of the 3' 513-base untranslated region of the mouse NfkBia gene (see Reference Example 8); and a sequence from nucleotides 71 to 112 (SEQ ID NO: 16) in AI462015 quantified using mouse GENECHIP® was confirmed as a transcript in CHO cells).

Thus, the expression level of NfkBia mRNA was quantified in the highly AI462015-expressing cells with the high potential to produce mAbs to confirm that the expression was suppressed.

Figure 11:
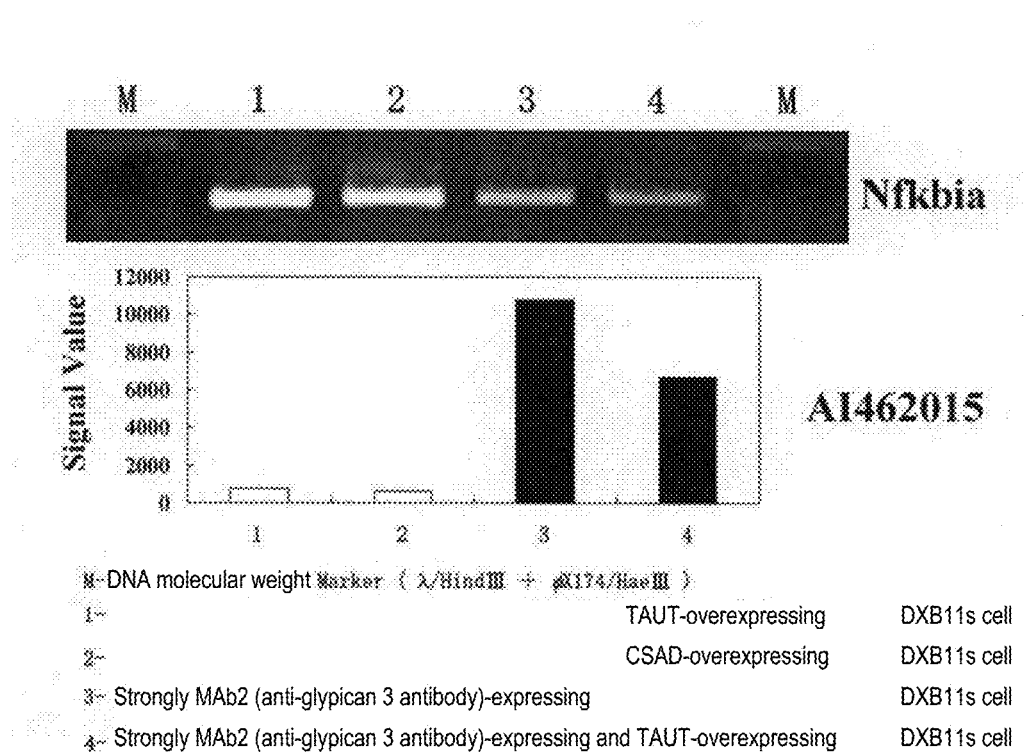
FIG. 11 shows the strong expression of the transcript AI462015 and suppressed NfkBia expression in highly antibody-producing cells (Reference Example 4).

Since the sequence of NfkBia mRNA in CHO cells was unknown, probes (5' ACTTGGTGACTTTGGGTGCT and 5' GCCTCCAAACACACAGTCAT) (SEQ ID NOs: 17 and 18) were designed from sequences conserved in mouse and rat amino acid coding regions (for both, 942 bases: 314 amino acids) to produce a 325-bp PCR product. The 325-bp PCR clone is considered as a partial sequence of CHO cell-derived NfkBia mRNA, in light of its sequence homology (FIG. 11).

Figure 13:
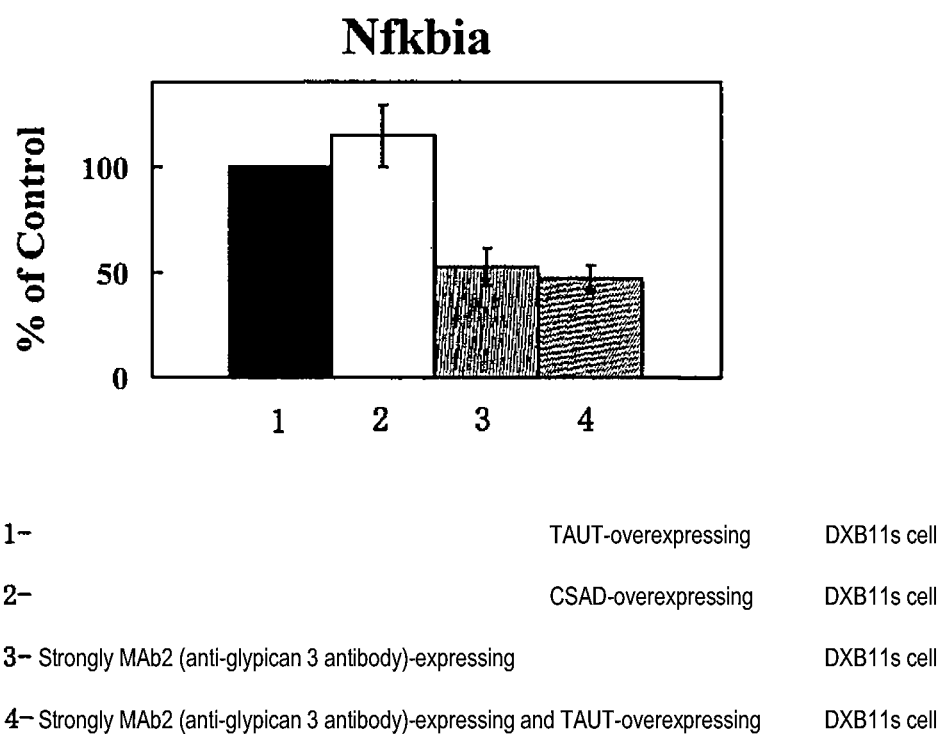
FIG. 13 shows results of quantifying suppressed NfkBia expression in highly antibody-producing cells (Reference Example 4).

Mouse Genome 430 2.0 Array (Reference Example 1) was unable to quantify the expression of NfkBia mRNA, probably because the probe sequence corresponded to a species-specific sequence in CHO cells. The comparison of the 325-bp PCR product levels showed that the NfkBia mRNA expression was suppressed in the highly mAb-producing cells that overexpressed the AI462015 sequence (Lanes 3 and 4) compared with gene-overexpressing cells that produced no mAb (Lanes 1 and 2). TAQMAN® Probe Set (FIG. 12) capable of quantifying a partial sequence of the 325-bp product was further designed and used in RT-PCR quantification. As a result, the NfkBia mRNA expression in the highly mAb-producing cells was suppressed to approximately 50% of the level in the cells that produced no mAb (FIG. 13).

These results suggest that the expression of NfkBia mRNA is suppressed in the highly mAb-producing cells, resulting in their enhanced potential to produce mAbs. The promoter/enhancer regions in the expression plasmids used by the present inventors for mAb gene expression actually contained two or more NfkB-binding sites (FIG. 14; the NfkB-binding sites on the mouse MCMV IE2 promoter). These enhancer regions are essential for the high expression of mAb genes. It therefore appears that the high mAb production is brought about in part by the following event: NfkB activated by the suppression of the NfkBia expression is translocated into the nucleus so that the promoter activity is enhanced.

Reference Example 5

Analysis of microRNA Increased in Highly Antibody-Producing CHO Cell

Figure 15:
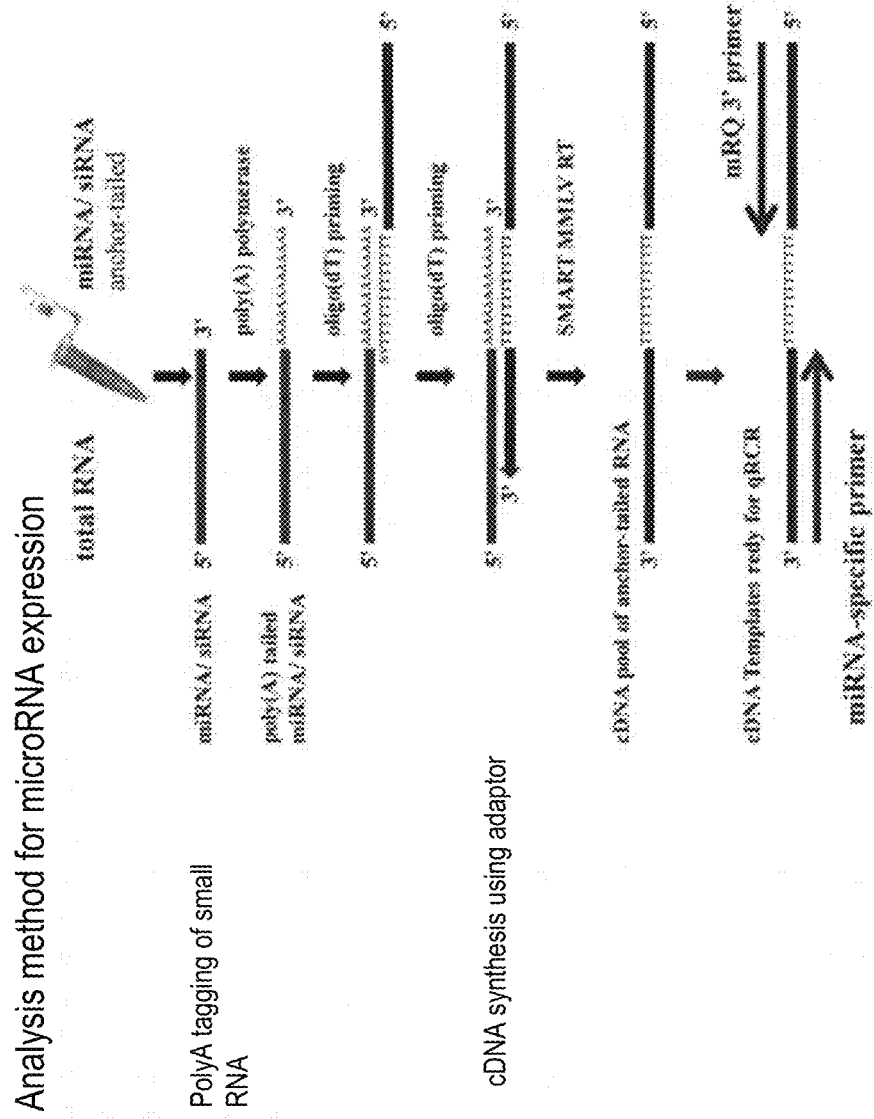
FIG. 15 summarizes an analysis method for microRNA expression (Reference Example 5).
Figure 16:
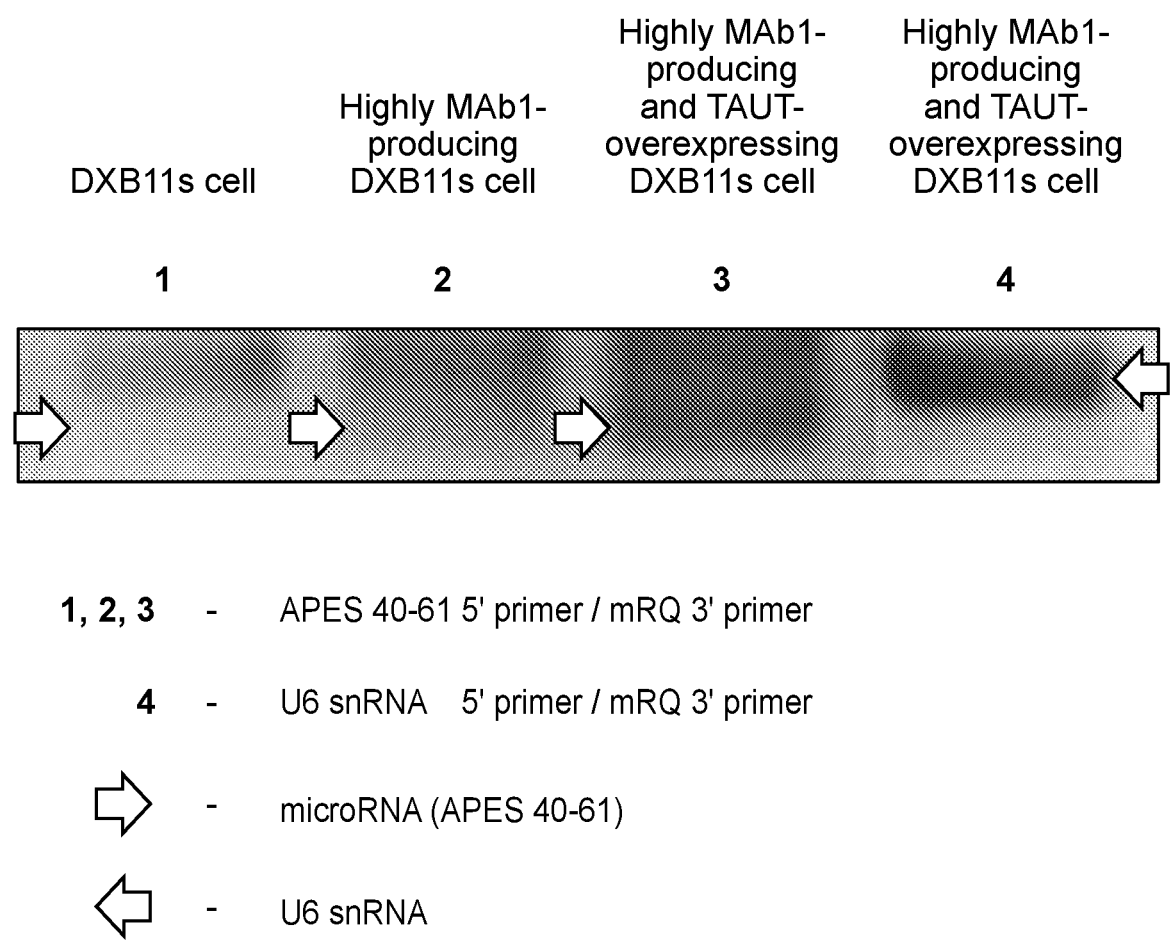
FIG. 16 shows PCR products derived from microRNAs highly expressed in highly antibody-producing cells (Reference Example 5).

As shown in FIG. 15, Mir-X™ miRNA First-Strand Synthesis Kit (Clontech Laboratories, Inc.) was used to analyze microRNAs. Small RNAs prepared from the highly MAb1 (anti-IL-6R antibody)-producing DXB11s cells and the highly MAb1 (anti-IL-6R antibody) producing and TAUT-overexpressing DXB11s cells during subculture and from DXB11s host cells before mAb gene transfer were 3'-tagged with poly(A) and then primed with an adaptor having oligo dT at the 3' end and a PCR primer sequence (mRQ 3' primer) at the 5' end to synthesize primary-strand cDNAs. qPCR reaction (95° C. for 5 sec and 60° C. for 20 sec, 30 cycles) was carried out using the obtained cDNAs as templates, the mRQ 3' primer, an expected APES sequence-derived microRNA-specific primer (APES 40-61 5' primer or APES 71-91 5' primer), and further, U6 snRNA 5' primer as a positive control. The PCR reaction solutions were purified and then electrophoresed on 3% agarose gel. As shown in FIG. 16, bands having the size of interest were detected by the PCR reaction using the APES 40-61 5' primer and the U6 snRNA 5' primer. As shown in Lanes 1, 2, and 3, the 22-base APES 40-61 (AAGTACCAAAATAAT-TACCAAC: SEQ ID NO: 10) was highly expressed in the highly MAb1 (anti-IL-6R antibody)-producing cells. The expression level of the positive control U6 snRNA (Lane 4) was comparable among all of these cell lines, and the presence of APES 71-91 (CATATACAACATTTA-CAAGAA: SEQ ID NO: 15) was not confirmed (data not shown), suggesting that the APES 40-61 sequence (22 bases) conserved regardless of species contributes as a microRNA to higher antibody production.

Reference Example 6

Figure 17:
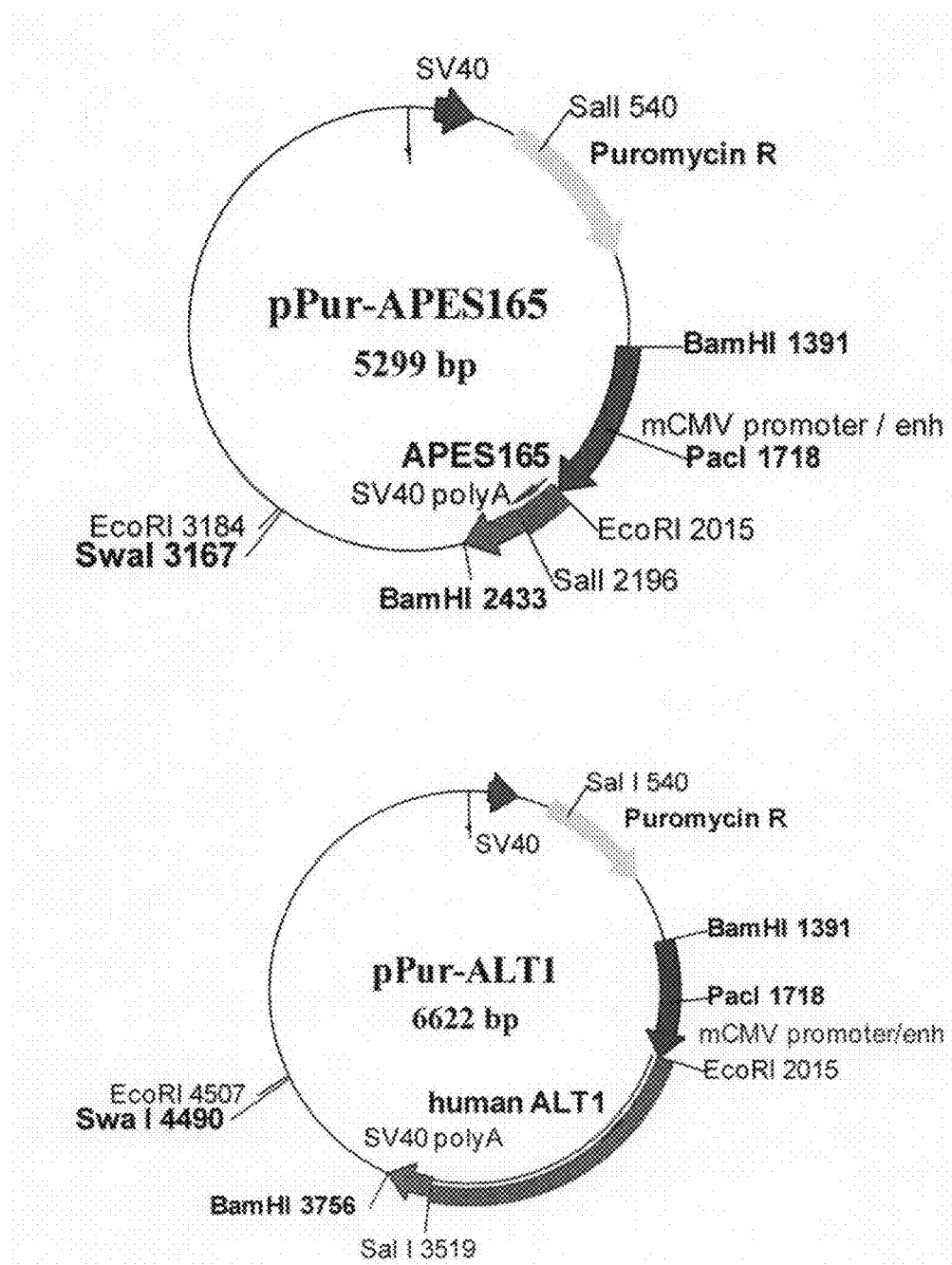
FIG. 17 shows plasmids pPur-APES165 and pPur-ALT1 that were used for the co-expression of the partial sequence 165 bp of the transcript AI642048 (437b) and the co-expression of ALT1, respectively, in pHyg-TAUT-expressing cells (Reference Example 6).
Figure 19:
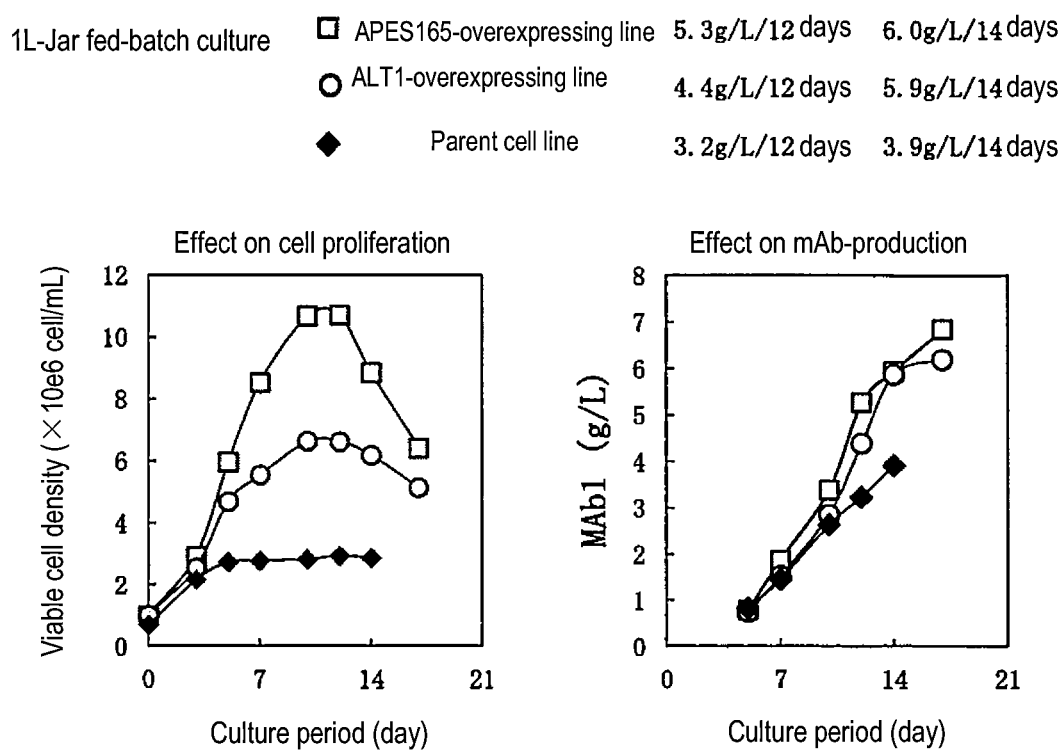
FIG. 19 shows results of 1 L-jar fed-batch culture, showing the effects on higher cell proliferation and on higher mAb-production brought about by the overexpression of APES (Reference Example 6).

Example of Higher Growth Resulting from APES Overexpression in Host Cell for Antibody Production Highly mAb-producing cells (DXB11/TAUT/MAb1) that produced 3.9 g/L of Mab1 (anti-IL-6R antibody) on day 14 of the 1 L-jar fed-batch culture were obtained from the host cells DXB11/TAUT for mAb production. By virtue of the ability of TAUT to maintain survival rates, the cells produced 8.1 g/L on day 31 of the culture. High production on day 14 of the culture, however, required increasing the maximum viable cell density reached by the cells (4.1×10e6 cells/mL), in consideration of actual production. If the suppressed Nfkbia mRNA expression resulting from the overexpression of APES (Reference Example 4) promoted the activation of Nfkb, the expression of growth-related genes would be increased; thus, the maximum viable cell density reached by the cells might be increased. A plasmid for the co-overexpression of APES and a plasmid for the co-overexpression of ALT1, which contributed to higher mAb production as with APES (pPur-APES165 and pPur-ALT1, respectively; FIG. 17) were each transferred to the highly mAb-producing cells DXB11/TAUT/MAb1 (parent line). The top three highly proliferative lines were selected for each of the two types and subjected to shaker feeding fed-batch culture. As a result, the average maximum viable cell density reached by the cells was (11.5±1.7)×10e6 cells/mL for the APES165-overexpressing cells, showing that cells more highly proliferative than the ALT1-overexpressing cells ((8.9±1.8)×10e6 cells/mL were obtained. The average mAb yield on day 14 of the shaker fed-batch culture was 4.4±0.6 g/L for the APES-overexpressing cells and 4.0±0.6 g/L for the ALT1-overexpressing cells, which were higher than 3.4 g/L for the DXB11/TAUT/MAb1 cells without transfer, showing that the effect of APES overexpression positively acts independently of the effect of TAUT overexpression (FIG. 18). The positive effect brought about by the overexpression of APES was markedly observed in the 1 L-jar fed-batch culture. The comparison of the highly proliferative cells in the shaker fed-batch culture revealed that the APES-overexpressing cell line was most highly proliferative and advantageously exhibited, even by a short-term culture, a yield as high as 5.3 g/L on day 12 of the culture relative to 3.2 g/L for the parent cell line and 4.4 g/L for the ALT1-overexpressing cell line (FIG. 19). On the basis of these results, a APES165-overexpressing host DXB11/TAUT/APES was prepared in order to modify the host cells DXB11/TAUT for mAb production into more highly proliferative host cells. The pPur-APES165 was transferred to the DXB11/TAUT host by electroporation. After drug selection, the expression level of APES snRNA (small non-coding RNA) at the time of subculture was quantified for 9 lines of candidate hosts having a favorable survival rate and favorable growth. The DXB11/TAUT/APES candidate host cell line having a high APES expression level was shown to have a high viable cell density during culture and exhibit a correlation ($R^2$=0.70) (FIG. 20).

Reference Example 7

Example of Higher Production Resulting from APES Overexpression in mAb-Producing Cell—2

In the same way as in Reference Example 3, plasmids for the expression of the 5' partial sequence of the AI462015 transcript were transferred to strongly MAb1-expressing DXB11s cells, and the potential to produce antibodies was compared among the lines.

Figure 21:
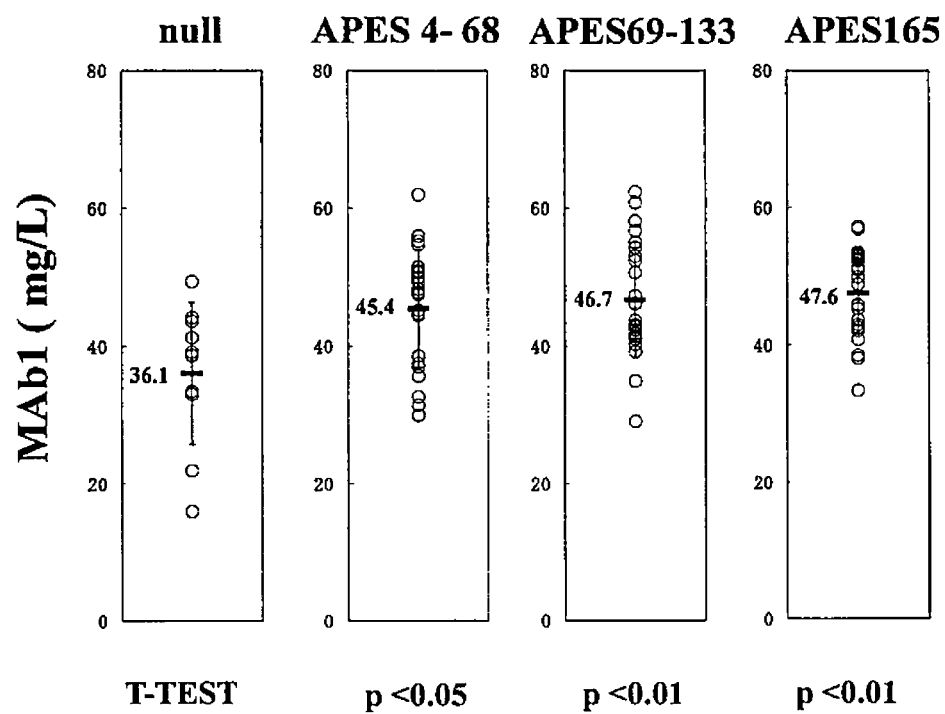
FIG. 21 shows that the MAb1 yield is increased by the overexpression of a partial sequence of the partial sequence APES165 of the transcript AI462015 (437b) (Reference Example 7).

In addition to APES4-168 (APES165), expression units of APES4-68 (SEQ ID NO: 5) and APES69-133 (SEQ ID NO: 6), each of which consisted of a partial sequence thereof, were prepared to study the potential of the cells to produce antibodies. Compared with strong null vector expression (null), APES4-68 and APES69-133 exhibited high mAb production with significant differences of $p<0.05$ and $p<0.01$, respectively (t-test, $P<0.001$, FIG. 21).

Figure 22:
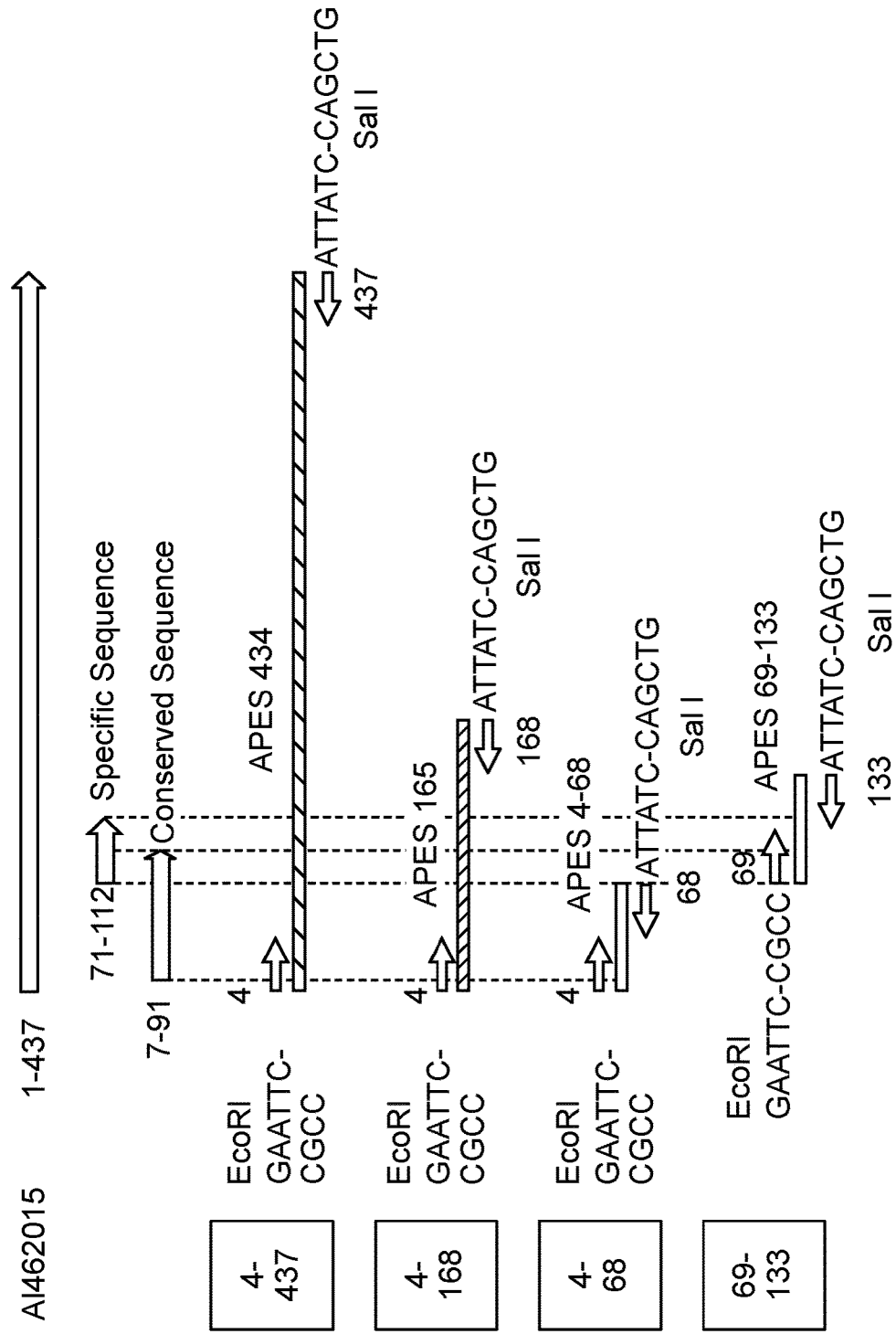
FIG. 22 shows that the partial sequence of APES165 found to have a high mAb-producing effect in FIG. 21 comprises an Nfkbia complementary sequence (Reference Example 7).

FIG. 22 shows the positions, in the mouse AI462015 transcript, of the partial sequences that exhibited APES activity, which were identified in Reference Example 3 and this Reference Example. These partial sequences that exhibited APES activity contained a 23-base or longer complementary sequence of Nfkbia.

The present invention is applicable to cells producing any recombinant polypeptide (e.g., any recombinant antibody).

All publications, patents, and patent applications cited herein are incorporated herein by reference in their entirety.

The invention claimed is:

1. A method for preparing a cell line that stably expresses two or more foreign genes, said method comprising:
   a) introducing into a cell a first foreign nucleic acid sequence encoding a first foreign protein and a nucleic acid sequence that is a protein-non-coding RNA encoding a protein such that the first foreign protein and the non-coding RNA encoding a protein are expressed; and
   b) introducing into the cell a second nucleic acid encoding a second foreign protein,
   wherein the first and second foreign proteins are difficult to express at the same time into the cell without introducing the nucleic acid sequence that is a non-coding RNA,
   thereby preparing a cell line that stably expresses the non-coding RNA protein, the first foreign protein and the second foreign protein,
   wherein the nucleic acid sequence that is a protein-non-coding RNA consists of the nucleic acid sequence as set forth in SEQ ID NO: 2 or a complementary sequence thereof,
   wherein the first nucleic acid sequence encoding the first foreign protein is a taurine transporter (TAUT) protein, and
   wherein the first foreign nucleic acid sequence, the nucleic acid sequence that is a protein-non-coding RNA and the second foreign nucleic acid sequence are introduced into the cell by an expression vector.

2. A method for preparing a cell line that stably expresses two or more foreign genes, said method comprising:
   a) introducing into a cell a first foreign nucleic acid sequence encoding a first foreign protein and a nucleic acid sequence that is a protein-non-coding RNA encoding a protein such that the first foreign protein and the non-coding RNA encoding a protein are expressed; and
   b) introducing into the cell a second nucleic acid encoding a second foreign protein, and
   c) introducing into the cell a third nucleic acid encoding a third foreign protein,
   wherein the first, second and third foreign proteins are difficult to express at the same time into the cell without introducing the nucleic acid sequence that is a non-coding RNA,
   thereby preparing a cell line that stably expresses the non-coding RNA protein, the first, second and third foreign proteins, wherein the nucleic acid sequence that is a protein-non-coding RNA consists of the nucleic acid sequence as set forth in SEQ ID NO: 2 or a complementary sequence thereof, wherein the first nucleic acid sequence encoding the first foreign protein is a taurine transporter (TAUT) protein, and wherein the first foreign nucleic acid sequence, the nucleic acid sequence that is a protein-non-coding RNA, the second and third foreign nucleic acid sequences are introduced into the cell by an expression vector.

3. The method according to claim 1, wherein a gene of a desired protein is further introduced into the cell to prepare a host cell line for the production of the desired protein.

4. The method according to claim 2, wherein a gene of a desired protein is further introduced into the cell to prepare a host cell line for production of the desired protein.

\* \* \* \* \*

SEQUENCE LISTING

<160> NUMBER OF SEQ ID NOS: 48

<210> SEQ ID NO 1
<211> LENGTH: 437
<212> TYPE: DNA
<213> ORGANISM: Mus musculus

<400> SEQUENCE: 1

```
tttgtctgta aaatctgtt taataaatat acatcttaga agtaccaaaa taattaccaa    60
caaaatacaa catatacaac atttacaaga aggcgacaca gaccttagtt ggggcgact   120
tttaagcaca tgccactgaa cacctggctc ttacatggga ggacacactg gctcactta   180
ctaggtctat ggtggttcaa tcaaaagcac aataaataaa acgtggtcct ttcattaggt   240
tctggaaaat cacctccccc cccccaaaa aaatcccac aaacatgaac cttaagagac    300
attttctttg aatttcagtg atctgtttcc ccggatttca caaagacaac agccgaatca   360
ccccagtaaa atgcctgggt ctaggcgctg tgtggtgtgg tgctaagtat accctttctc   420
atttttttc ttttct                                                   437
```

<210> SEQ ID NO 2
<211> LENGTH: 165
<212> TYPE: DNA
<213> ORGANISM: Artificial Sequence
<220> FEATURE:
<223> OTHER INFORMATION: Description of Artificial Sequence: Synthetic
      APES165 polynucleotide

<400> SEQUENCE: 2

```
gtctgtaaaa atctgtttaa taaatataca tcttagaagt accaaaataa ttaccaacaa    60
aatacaacat atacaacatt tacaagaagg cgacacagac cttagttggg ggcgactttt   120
aagcacatgc cactgaacac ctggctctta catgggagga cacac                   165
```

<210> SEQ ID NO 3
<211> LENGTH: 434
<212> TYPE: DNA
<213> ORGANISM: Artificial Sequence
<220> FEATURE:
<223> OTHER INFORMATION: Description of Artificial Sequence: Synthetic
      APES434 polynucleotide

<400> SEQUENCE: 3

```
gtctgtaaaa atctgtttaa taaatataca tcttagaagt accaaaataa ttaccaacaa    60
aatacaacat atacaacatt tacaagaagg cgacacagac cttagttggg ggcgactttt   120
aagcacatgc cactgaacac ctggctctta catgggagga cacactgggc tcacttacta   180
ggtctatggt ggttcaatca aaagcacaat aaataaaacg tggtcctttc attaggttct   240
ggaaaatcac ctccccccccc cccaaaaaaa atcccacaaa catgaacctt aagagacatt   300
tctttgaat tcagtgatc tgtttccccg gatttcacaa agacaacagc cgaatcaccc    360
cagtaaaatg cctgggtcta ggcgctgtgt ggtgtggtgc taagtatacc ctttctcatt   420
ttttttcttt ttct                                                    434
```

<210> SEQ ID NO 4
<211> LENGTH: 130
<212> TYPE: DNA
<213> ORGANISM: Artificial Sequence
<220> FEATURE:
<223> OTHER INFORMATION: Description of Artificial Sequence: Synthetic
      APES130 polynucleotide

<400> SEQUENCE: 4

```
gtctgtaaaa atctgtttaa taaatataca tcttagaagt accaaaataa ttaccaacaa    60
aatacaacat atacaacatt tacaagaagg cgacacagac cttagttggg ggcgactttt   120
aagcacatgc                                                         130
```

```
<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      APES 4-68 oligonucleotide

<400> SEQUENCE: 5
gtctgtaaaa atctgtttaa taaatataca tcttagaagt accaaaataa ttaccaacaa      60
aatac                                                                 65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      APES 69-133 oligonucleotide

<400> SEQUENCE: 6
aacatataca acatttacaa gaaggcgaca cagaccttag ttgggggcga cttttaagca      60
catgc                                                                 65

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      APES 40-91 oligonucleotide

<400> SEQUENCE: 7
aagtaccaaa ataattacca acaaaataca acatatacaa catttacaag aa              52

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      APES 40-68 oligonucleotide

<400> SEQUENCE: 8
aagtaccaaa ataattacca acaaaatac                                       29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      APES 40-63 oligonucleotide

<400> SEQUENCE: 9
aagtaccaaa ataattacca acaa                                            24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      APES 40-61 oligonucleotide
```

<210> SEQ ID NO 10

```
<400> SEQUENCE: 10
aagtaccaaa ataattacca ac                                              22
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      APES 69-91 oligonucleotide

```
<400> SEQUENCE: 11
aacatataca acatttacaa gaa                                             23
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 84-104 oligonucleotide

```
<400> SEQUENCE: 12
tacaagaagg cgacacagac c                                               21
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      APES 99-119 oligonucleotide

```
<400> SEQUENCE: 13
acagacctta gttgggggcg ac                                              22
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 101-121 oligonucleotide

```
<400> SEQUENCE: 14
gaccttagtt gggggcgact t                                               21
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 71-91 oligonucleotide

```
<400> SEQUENCE: 15
catatacaac atttacaaga a                                               21
```

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      APES 71-112 oligonucleotide

<400> SEQUENCE: 16
catatacaac atttacaaga aggcgacaca gaccttagtt gg         42

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
acttggtgac tttgggtgct         20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcctccaaac acacagtcat         20

<210> SEQ ID NO 19
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide-part of Hamster Nfkbia mRNA

<400> SEQUENCE: 19
agtacccgga tacagcagca gctgggccag ctgacccggg aaaatcttca gatgctgccc         60
gagagtgagg atgaggagag ctacgacaca gagtcagaat tcacggagga tgagctgccc        120
tatgatgact gtgtgtttgg aggca         145

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cagctgaccc gggaaaatc         19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgactctgtg tcgtagctct cctc         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tcagatgctg cccgagagtg agga                                              24

<210> SEQ ID NO 23
<211> LENGTH: 1394
<212> TYPE: DNA
<213> ORGANISM: Mus musculus

<400> SEQUENCE: 23
ctctgggctc gaatggcatg ggggacagct tttatatggt taactccgcc cgttttatga       60
ctagaaccaa tagttttaa tgccaaatgc actgaaatcc cctaatttgc aaagccaaac       120 gcccccctatg tgagtaatac ggggactttt tacccaattt cccaagcgga aagcccccta    180
atacactcat atggcatatg aatcagcacg gtcatgcact ctaatggcgg cccataggga      240 cttttccacat aggggcgtt caccatttcc cagcataggg gtggtgactc aatggccttt      300
acccaagtac attgggtcaa tgggaggtaa gccaatgggt ttttcccatt actggcaagc      360
acactgagtc aaatgggact ttccactggg ttttgcccaa gtacattggg tcaatgggag      420
gtgagccaat gggaaaaacc cattgctgcc aagtacactg actcaatagg gactttccaa      480
tgggtttttc cattgttggc aagcatataa ggtcaatgtg ggtgagtcaa tagggacttt      540
ccattgtatt ctgcccagta cataaggtca ataggggtg aatcaacagg aaagtcccat       600
tggagccaag tacactgcgt caataggac tttccattgg gttttgccca gtacataagg       660 tcaataggg atgagtcaat gggaaaaacc cattggagcc aagtacactg actcaatagg       720
gactttccat tgggttttgc ccagtacata gggtcaatag gggtgagtc aacaggaaag       780 ttccattgga gccaagtaca ttgagtcaat agggactttc caatgggttt tgcccagtac      840
ataaggtcaa tgggaggtaa gccaatgggt ttttcccatt actggcacgt atactgagtc      900
attagggact ttccaatggg ttttgcccag tacataaggt caataggggt gaatcaacag      960
gaaagtccca ttggagccaa gtacactgag tcaatagga ctttccattg gttttgccc      1020 agtacaaaag gtcaataggg ggtgagtcaa tgggttttc ccattattgg cacgtacata     1080
aggtcaatag gggtgagtca ttgggttttt ccagccaatt taattaaaac gccatgtact    1140
ttcccaccat tgacgtcaat gggctattga aactaatgca acgtgacctt taaacggtac    1200
tttcccatag ctgattaatg ggaaagtacc gttctcgagc caatacacgt caatgggaag    1260
tgaaagggca gccaaaacgt aacaccgccc cggttttccc ctggaaattc catattggca    1320
cgcattctat tggctgagct gcgttctacg tgggtataag aggcgcgacc agcgtcggta    1380
ccgtcgcagt cttg                                                       1394

<210> SEQ ID NO 24
<211> LENGTH: 24
<212> TYPE: DNA
<213> ORGANISM: Homo sapiens

<400> SEQUENCE: 24
ttgttggtaa ttattttggt actt                                              24

<210> SEQ ID NO 25
<211> LENGTH: 433
<212> TYPE: DNA
<213> ORGANISM: Mus musculus

<400> SEQUENCE: 25

```
tgtctgtaaa aatctgttta ataaatatac atcttagaag taccaaaata attaccaaca      60
aaatacaaca tatacaacat ttacaagaag gcgacacaga ccttagttgg gggcgacttt     120
taagcacatg ccactgaaca cctggctctt acatgggagg acacactggg ctcacttact     180
aggtctatgg tggttcaatc aaaagcacaa taaataaaac gtggtccttt cattaggttc     240
tggaaaatca cctccccccc ccccaaaaaa aatcccacaa acatgaacct taagagacat     300
tttctttgaa tttcagtgat ctgtttcccc ggatttcaca aagacaacag ccgaatcacc     360
ccagtaaaat gcctgggtct aggcgctgtg tggtgtggtg ctaagtatac cctttctcat     420
ttttttctt ttt                                                         433
```

<210> SEQ ID NO 26
<211> LENGTH: 414
<212> TYPE: DNA
<213> ORGANISM: Cricetulus griseus

<400> SEQUENCE: 26

```
tgtctgtaaa aatctgttta ataaatatac atcttagaag taccaaaata attaccaaca      60
aaatacacca tatacaacat ttacaagagg gtaacaaaaa cctcagtcgg gagtgactag     120
cacataccac tcaacacctg gttctacatg tgaggacata ccaggctcag ctaccagatc     180
taccgttcag tcaaaagcac aataaataga atgtggtccc tttcatcagt ctggaaaacc     240
acctcccaaa acctcacgaa tgtgagcttt aaaagacatt ttctttgaat tccaatgatc     300
tgtttcccca tttcacaaaa ataacaatct gccatcacca gagtaagatg cttgggggca     360
ggctgtgtgc agtgtggtgg taagtatatc cctttctttc tttttttct tctt            414
```

<210> SEQ ID NO 27
<211> LENGTH: 414
<212> TYPE: DNA
<213> ORGANISM: Cricetulus griseus

<400> SEQUENCE: 27

```
aagaagaaaa aaagaaaga aagggatata cttaccacca cactgcacac agcctgcccc      60
caagcatctt actctggtga tggcagattg ttatttttgt gaaatgggga aacagatcat     120
tggaattcaa agaaaatgtc ttttaaagct cacattcgtg aggttttggg aggtggtttt     180
ccagactgat gaaagggacc acattctatt tattgtgctt ttgactgaac ggtagatctg     240
gtagctgagc ctggtatgtc ctcacatgta gaaccaggtg ttgagtggta tgtgctagtc     300
actcccgact gaggttttg ttaccctctt gtaaatgttg tatatggtgt atttgttgg      360
taattatttt ggtacttcta agatgtatat ttattaaaca gatttttaca gaca           414
```

<210> SEQ ID NO 28
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide-part of Hamster Nfkbis mRNA (134bp)

<400> SEQUENCE: 28

```
agtacccgga tacagcagca gctgggccag ctgacccggg aaaatcttca gatgctgccc      60
gagagtgagg atgaggagag ctacgacaca gagtcagaat tcacggagga tgagctgccc     120
tatgatgact gtgt                                                       134
```

-continued

```
<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: Synthetic
      conserved oligonucleotide 7-91

<400> SEQUENCE: 29
tgtaaaaatc tgtttaataa atatacatct tagaagtacc aaaataatta ccaacaaaat    60
acaacatata caacatttac aagaa                                          85

<210> SEQ ID NO 30
<211> LENGTH: 83
<212> TYPE: DNA
<213> ORGANISM: Homo sapiens

<400> SEQUENCE: 30
tgtaaaaatc tgtttaataa atatacatca taaaagtacc aaaataatta ccaacaatac    60
attatgtaca ccatttacag gag                                            83

<210> SEQ ID NO 31
<211> LENGTH: 85
<212> TYPE: DNA
<213> ORGANISM: Rattus norvegicus

<400> SEQUENCE: 31
tgtaaaaatc tgtttaataa atatacatct tagaagtacc aaaataatta ccaacaaaat    60
acaccatata caacatttac aagaa                                          85

<210> SEQ ID NO 32
<211> LENGTH: 89
<212> TYPE: DNA
<213> ORGANISM: Pan troglodytes

<400> SEQUENCE: 32
tgtaaaaatc tgtttaataa atatacatca taaaagtacc aaaataatta ctaacaatac    60
attatgtaca tcatttacag gagggtaac                                      89

<210> SEQ ID NO 33
<211> LENGTH: 89
<212> TYPE: DNA
<213> ORGANISM: Macaca mulatta

<400> SEQUENCE: 33
tggaaaaatc tgtttaataa atatacataa taaaagtacc aaaataatta ccaacaatac    60
actatgtaca ccatttacag aagggtaac                                      89

<210> SEQ ID NO 34
<211> LENGTH: 90
<212> TYPE: DNA
<213> ORGANISM: Bos taurus

<400> SEQUENCE: 34
tgtaaaaatc tgtttaataa atatacatct taaaagtacc aaaataatta ctgacaaaat    60
acactatgta cactatttac aggagggggaa                                    90

<210> SEQ ID NO 35
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      kB motif oligonucleotide

<400> SEQUENCE: 35
gggactttcc                                                            10

<210> SEQ ID NO 36
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
agtacccgga tacagcagca gctgggccag ctgacccggg aaaatcttca gatgctgccc     60
gagagtgagg atgaggagag ctacgacaca gagtcagaat tcacggagga tgagctgccc    120
tatgatgact gtgt                                                      134

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaattccgcc                                                            10

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
attatccagc tg                                                         12

<210> SEQ ID NO 39
<211> LENGTH: 437
<212> TYPE: DNA
<213> ORGANISM: Mus musculus

<400> SEQUENCE: 39
tttgtctgta aaatctgtt taataaatat acatcttaga agtaccaaaa taattaccaa      60
caaaatacaa catatacaac atttacaaga aggcgacaca gaccttagtt ggggcgact     120 tttaagcaca tgccactgaa cacctggctc ttacatggga ggacacactg gctcactta    180 ctaggtctat ggtggttcaa tcaaaagcac aataaataaa acgtggtcct ttcattaggt   240
tctggaaaat cacctccccc cccccaaaa aaaatcccac aaacatgaac cttaagagac    300
attttctttg aatttcagtg atctgtttcc ccggatttca caaagacaac agccgaatca   360
ccccagtaaa atgcctgggt ctaggcgctg tgtggtgtgg tgctaagtat accctttctc   420 atttttttc ttttttct                                                  437
```

<210> SEQ ID NO 40
<211> LENGTH: 433
<212> TYPE: DNA
<213> ORGANISM: Mus musculus

<400> SEQUENCE: 40

```
tgtctgtaaa aatctgttta ataaatatac atcttagaag taccaaaata attaccaaca    60
aaatacaaca tatacaacat ttacaagaag gcgacacaga ccttagttgg gggcgacttt   120
taagcacatg ccactgaaca cctggctctt acatgggagg acacactggg ctcacttact   180
aggtctatgg tggttcaatc aaaagcacaa taaataaaac gtggtccttt cattaggttc   240
tggaaaatca cctcccccc ccccaaaaaa atcccacaa acatgaacct taagagacat     300
tttctttgaa tttcagtgat ctgtttcccc ggatttcaca aagacaacag ccgaatcacc   360
ccagtaaaat gcctgggtct aggcgctgtg tggtgtggtg ctaagtatac cctttctcat   420
tttttttctt ttt                                                      433
```

<210> SEQ ID NO 41
<211> LENGTH: 83
<212> TYPE: DNA
<213> ORGANISM: Homo sapiens

<400> SEQUENCE: 41

```
tgtaaaaatc tgtttaataa atatacatca taaaagtacc aaaataatta ccaacaatac    60
attatgtaca ccatttacag gag                                           83
```

<210> SEQ ID NO 42
<211> LENGTH: 85
<212> TYPE: DNA
<213> ORGANISM: Rattus norvegicus

<400> SEQUENCE: 42

```
tgtaaaaatc tgtttaataa atatacatct tagaagtacc aaaataatta ccaacaaaat    60
acaccatata caacatttac aagaa                                         85
```

<210> SEQ ID NO 43
<211> LENGTH: 89
<212> TYPE: DNA
<213> ORGANISM: Pan troglodytes

<400> SEQUENCE: 43

```
tgtaaaaatc tgtttaataa atatacatca taaaagtacc aaaataatta ctaacaatac    60
attatgtaca tcatttacag gagggtaac                                     89
```

<210> SEQ ID NO 44
<211> LENGTH: 89
<212> TYPE: DNA
<213> ORGANISM: Macaca mulatta

<400> SEQUENCE: 44

```
tggaaaaatc tgtttaataa atatacataa taaaagtacc aaaataatta ccaacaatac    60
actatgtaca ccatttacag aagggtaac                                     89
```

<210> SEQ ID NO 45
<211> LENGTH: 90
<212> TYPE: DNA
<213> ORGANISM: Bos taurus

```
<400> SEQUENCE: 45
tgtaaaaatc tgtttaataa atatacatct taaaagtacc aaaataatta ctgacaaaat    60
acactatgta cactatttac aggaggggaa                                    90

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaaaaaaaa aaa                                                      13

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 47
tttttttttt tttvn                                                    15

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttttttttt ttt                                                      13
```